US012527389B2

(12) United States Patent
Koh et al.

(10) Patent No.: US 12,527,389 B2
(45) Date of Patent: Jan. 20, 2026

(54) SELECTION OF A CHEMICAL COMPOUND APPLICABLE ON A CLASS OF HUMAN HAIRS

(71) Applicant: Wella Germany Gmbh, Darmstadt (DE)

(72) Inventors: Angel Koh, Shinjuku-ku Tokyo (JP); Hui Min Lee, Shinjuku-ku Tokyo (JP); Chun Wei Tan, Shinjuku-ku Tokyo (JP); Max Morini, Darmstad (DE)

(73) Assignee: Wella Germany Gmbh, Darmstadt (DE)

( * ) Notice: Subject to any disclaimer, the term of this patent is extended or adjusted under 35 U.S.C. 154(b) by 0 days.

(21) Appl. No.: 18/613,558

(22) Filed: Mar. 22, 2024

(65) Prior Publication Data

US 2024/0341450 A1 Oct. 17, 2024

Related U.S. Application Data

(63) Continuation of application No. 18/453,944, filed on Aug. 22, 2023.

(30) Foreign Application Priority Data

Nov. 11, 2022 (EP) .................................... 22207058

(51) Int. Cl.

*G16C 20/30* (2019.01)
*A45D 7/04* (2006.01)
(Continued)

(52) U.S. Cl.

CPC ............. *A45D 44/005* (2013.01); *A45D 7/04* (2013.01); *A45D 19/005* (2021.01); *A61B 5/448* (2013.01)

(58) Field of Classification Search

CPC ...... A45D 44/005; A45D 7/04; A45D 19/005; A61B 5/448; G16C 20/30; G16C 20/64; G16C 20/70; G16C 20/90

See application file for complete search history.

(56) References Cited

U.S. PATENT DOCUMENTS 8,092,553 B2 1/2012 Giafferi et al.
10,631,774 B2 * 4/2020 Iftikhar ................. G01N 33/68
(Continued)

FOREIGN PATENT DOCUMENTS

WO 2017079462 A1 5/2017
WO 2019222327 A1 11/2019

OTHER PUBLICATIONS

Search Report EP22207058 application mailed on Apr. 13, 2023.

*Primary Examiner* — Larry D Riggs, II
*Assistant Examiner* — Ghazal Sabour
(74) *Attorney, Agent, or Firm* — Dennemeyer & Associates LLC

(57) ABSTRACT

The disclosure notably relates to a computer-implemented method for selecting a chemical compound applicable on a class of human hairs. The method comprises obtaining a database storing data relative to chemical compounds. For each compound the data comprises an identifier, an ingredient and a performance score. The method also comprises obtaining assessed hair properties and hair target properties. The method also comprises computing at least one goal score and a manageability goal score from the assessed hair properties and hair target properties. The method also comprises determining at least one identifier in the database satisfying the computed goal score and the computed manageability goal score. The satisfying comprises minimizing a distance function between the computed goal score and a corresponding goal score and maximizing a fit-to-manageability function between the computed manageability goal (Continued)

score and the corresponding manageability score. The method also comprises outputting the determined at least one identifier.

8 Claims, 8 Drawing Sheets

(51) Int. Cl.

| | |
|---|---|
| ***A45D 19/00*** | (2006.01) |
| ***A45D 44/00*** | (2006.01) |
| ***A61B 5/00*** | (2006.01) |
| ***G16C 20/64*** | (2019.01) |
| ***G16C 20/70*** | (2019.01) |
| ***G16C 20/90*** | (2019.01) |

(56) References Cited

U.S. PATENT DOCUMENTS

| | | | | |
|---|---|---|---|---|
| 11,080,727 | B1 | 8/2021 | Novak et al. | |
| 11,282,190 | B2 | 3/2022 | Niebauer et al. | |
| 11,341,557 | B2 | 5/2022 | Cook et al. | |
| 2006/0265244 | A1* | 11/2006 | Baumann | A61B 5/441 424/59 |
| 2011/0313879 | A1 | 12/2011 | Mourad et al. | |
| 2013/0331342 | A1 | 12/2013 | Youngquist et al. | |
| 2017/0270679 | A1 | 9/2017 | Koven | |
| 2018/0125207 | A1 | 5/2018 | Shami | |
| 2021/0049514 | A1* | 2/2021 | Neumann | G06F 18/24 |
| 2024/0242258 | A1* | 7/2024 | Delapenha | G06Q 30/0621 |

* cited by examiner

300

| Compound Name | Anti-Dandruff | Color Protection | Volume | Repair | Hair Protection | Strengthening | Curl |
|---|---|---|---|---|---|---|---|
| Compound A | 0 | 0.2 | 0.6 | 0.2 | 0.2 | 0.6 | 0 |
| Compound B | 0 | 0 | 0.8 | 0 | 0 | 0 | 0 |
| Compound C | 0 | 0 | 0.8 | 0 | 0 | 0 | 0 |
| Compound D | 0 | 0 | 0.8 | 0 | 0 | 0 | 0 |
| Compound E | 0 | 0 | 0.8 | 0 | 0 | 0 | 0 |
| Compound F | 0 | 0 | 0.8 | 0 | 0 | 0 | 0 |
| Compound G | 0 | 0 | 1 | 0 | 0 | 0.4 | 0 |

310 320 330 340 350 360 370 380

FIG. 3

SELECTION OF A CHEMICAL COMPOUND APPLICABLE ON A CLASS OF HUMAN HAIRS

CROSS-REFERENCE TO RELATED APPLICATIONS

This is a Non-Provisional Utility Continuation Application, which claims priority to U.S. patent application Ser. No. 18/453,944 filed on Aug. 22, 2023 which claims priority to European Patent Office (EPO) application Ser. No. 22/207,058.3, filed Nov. 11, 2022, of which is hereby incorporated by reference in its entirety.

TECHNICAL FIELD

The disclosure relates to the field of computer programs and systems, and more specifically to a method, system and program for selecting a chemical compound applicable on a class of human hairs.

BACKGROUND

A number of products are available on the market to improve hair properties. Each product contains chemical compounds that are tailored to one or more properties of the hair, so that the improvement of a hair property can only be achieved if the right chemical compound is applied to the hair. Multiple factors play a role in the improvement of the hair's properties so that the chemical compound that is applied can be effective, for example the effectiveness of a chemical compound may depend on the thickness of the hair, its texture, but also the scalp on which the hair grows. In addition, the effectiveness of a chemical compound may also depend on the products that have been previously applied on the hair, i.e. the effectiveness of a compound in improving a hair property may be maximized if this compound is applied over or with another chemical compound. Thus, hair improvement depends on the application of the right chemical compounds selected based on multiple factors.

Systems and methods for selecting a product (such as shampoos) applicable on the hair are known, however these usually only take into account a user selection. This introduces user bias, which affects the selection of the product. Indeed, on one hand there are no guarantees that the selected product may yield desired results when applied to human hairs. On the other hand, the product corresponding to the user selection may not exist on the database, e.g., in the case of limited stock.

Within this context, there is still a need for an improved method for selecting a chemical compound applicable on a class of human hairs.

SUMMARY

It is therefore provided a computer-implemented method for selecting a chemical compound applicable on a class of human hairs. The class of human hairs is constrained by hair properties.

The method comprises obtaining a database storing data relative to chemical compounds applicable on the class of human hairs. For each compound the data comprises an identifier, an ingredient, and a performance score of the chemical compound when applied on human hairs. The performance score comprising a manageability score and a goal score.

The method also comprises obtaining, from user input, assessed hair properties and hair target properties.

The method also comprises computing at least one goal score and a manageability goal score from the assessed hair properties and hair target properties. The computed goal score and the computed manageability goal score thereby form a signature.

The method also comprises determining at least one identifier of a chemical compound stored in the database corresponding to a chemical compound satisfying the computed goal score and the computed manageability goal score. The satisfying comprises minimizing a distance function between the computed goal score and a corresponding goal score and maximizing a fit-to-manageability function between the computed manageability goal score and the corresponding manageability score.

The method also comprises outputting the determined at least one identifier of the chemical compound to be applied on the human hairs.

The method may comprise one or more of the following:

- the assessed hair properties and/or hair target properties comprise one or more of a hair type criterion such as straight hair, wavy hair, curly hair or coily hair, a hair length criterion such as short, medium or long, a hair condition criterion such as untreated, colored, permed or bleached hair, a hair feel criterion such as healthy or damaged hair, hair tool use criterion, a hair goal criterion such as color protection, repair, shine, smooth, a scalp condition criterion such as oily, dandruff, dry, a scalp goal criterion such as sebum control, anti-dandruff and moisturize, a hair texture criterion, a hair diameter criterion such as fine, medium and coarse, degree of damage criterion and/or an ethnicity criterion such as Latino, Caucasian, African American and/or Asian;
- the distance function is a function taking the computed goal score and the corresponding goal score as input, and outputting a decreasing value as the distance between the computed goal score and the corresponding goal score decreases;
- the chemical compounds applicable to human hairs comprise one or more of a shampoo compound and a hair conditioner compound, and wherein the distance function comprises one or more of:
  - a shampoo compound distance term of the type:

$$(\text{Cleansing Score}_{Product} - \text{Cleansing Score}_{Target})^2 + (\text{Shampoo Manageability}_{Product} - \text{Shampoo Manageability Score}_{Target})^2;$$

- a conditioner compound distance term of the type:

$$\text{Conditioner Manageability}_{Product} - \text{Conditioner Score}_{Target};$$

or

- a treatment distance term of the type:

$$\text{Treatment Manageability}_{Product} - \text{Treatment Score}_{Target};$$

wherein:

Cleansing $\text{Score}_{product}$, is a variable representing a value of a cleansing goal score by the chemical compound;

Shampoo $\text{Manageability}_{Product}$ is a variable representing a value of a goal score of a shampooing manageability by the chemical compound;

Treatment $\text{Manageability}_{Product}$ is a variable representing a value of a goal score of a treatment manageability by the chemical compound;

Cleansing $\text{Score}_{Target}$ is a variable representing a value of a cleansing goal score computed from the assessed hair properties;

Treatment $\text{Score}_{Target}$ is a variable representing a value of a treatment goal score computed from the assessed hair properties and hair target properties;

Shampoo $\text{ManageabilityScore}_{Target}$ is a variable representing a value of a shampoo manageability goal score computed from the assessed hair properties and hair target properties; and Conditioner $\text{Manageability}_{product}$ is a variable representing a value of a conditioner manageability goal score computed from the assessed hair properties and hair target properties;

the fit-to-manageability function is function of the type:

wherein:

$\text{Goal}_i$ is a value representing a goal score;

Goal $\text{Value}_{Product}$ is a variable representing a value of the performance score;

$\text{GoalThreshold}_i$ is a variable representing a value of a goal priority, varying between 0 to 1; and $\text{Weight}_i$ is a predetermined weight;

outputting the determined at least one identifier of the chemical compound further comprises displaying the at least one identifier of the chemical compound on a display engine;

further comprising applying the chemical compound on human hairs of a class corresponding to the assessed hair properties the chemical compound identified by the output, thereby reaching the hair target properties obtained from the user input; and the chemical compounds applicable on human hairs comprise one or more of a shampoo, a hair conditioner, a hair oil, a scalp tonic and/or serum.

It is further provided a computer program comprising instructions for performing the method.

It is further provided a computer readable storage medium having recorded thereon the computer program.

It is further provided a system comprising a processor coupled to a memory and a display device, the memory having recorded thereon the computer program.

$$\text{Fit (Manageability)} = \begin{cases} \left(\dfrac{\text{Manageability}_{Product} - LSL}{\text{Manageability Score} - LSL}\right)^{LP}, & \text{Manageability}_{Product} \le \text{Manageability Score} \\ \left(\dfrac{USL - \text{Manageability}_{Product}}{USL - \text{Manageability Score}}\right)^{UP}, & \text{Manageability}_{Product} > \text{Manageability Score} \end{cases},$$

wherein:

Manageability is a vector comprising $\text{Manageability}_{Product}$ variable and a Manageability Score variable, where $\text{Manageability}_{Product}$ is a variable representing a value of a manageability score by the chemical compound and a Manageability Score is a variable representing a value of a manageability goal score computed from the assessed hair properties and hair target properties; and LSL is a first variable and USL is a second variable;

LP is a lower exponent variable depending on user input and UP is an upper exponent variable depending on user input;

outputting the determined at least one identifier of the chemical compound comprises averaging the computed goal score and the computed manageability goal score, the at least one identifier of the chemical compound being ranked according a fit-to-goal distance to the average;

the fit-to-goal distance comprises a function of the type:

$$\text{Fit to goal} = \sum \text{Weight}_i \times \text{Goal}_i$$

where $\text{Goal}_i =$ $$\begin{cases} 0, \text{ Goal Value}_{Product} \le LSL \\ \dfrac{\text{Goal Value}_{Product}}{\text{Goal Threshold}_i}, \; LSL < \text{Goal Value}_{Product} < \text{Goal Threshold}_i; \\ 1, \text{ Goal Value}_{Product} \ge \text{Goal Threshold}_i \end{cases}$$

The processor operating with the display device to:

display a set of input interface screens;

for each displayed input interface screens, inputting by the user a value setting at least one hair property or hair target property; and displaying the outputted at least one identifier of the chemical compound to be applied on the human hairs.

The system may further comprise a camera configured to capture an image of a user's human hair, the processing unit being further configured to assess, from the captured image, the hair properties.

BRIEF DESCRIPTION OF THE DRAWINGS

Non-limiting examples will now be described in reference to the accompanying drawings, where:

FIGS. 3 to 8 show examples of the method.

DETAILED DESCRIPTION

Figure 1:
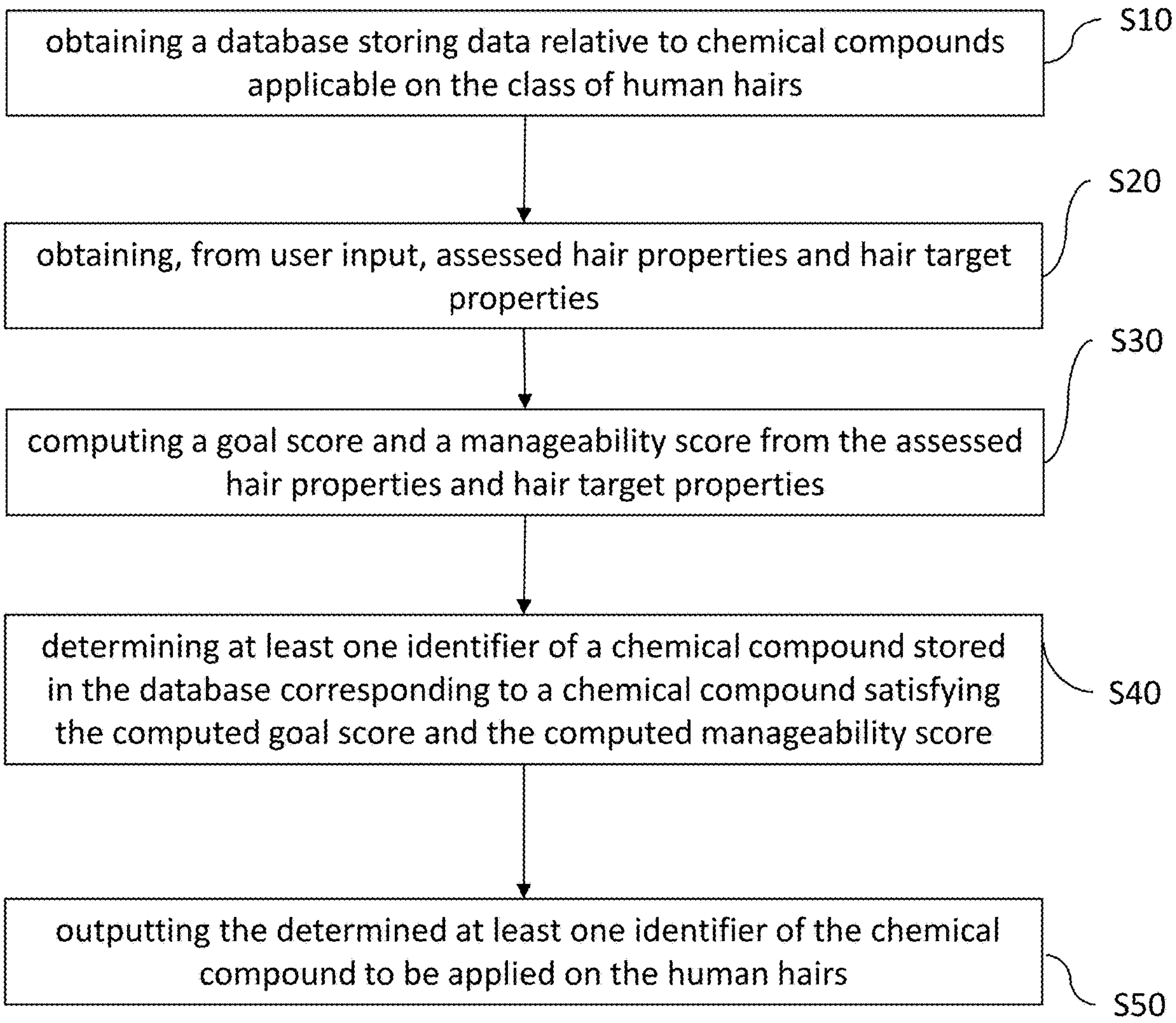
FIG. 1 shows a flowchart of an example of the method.

With reference to the flowchart of FIG. 1, it is proposed a computer-implemented method for selecting a chemical compound applicable on a class of human hairs, the class of human hairs being constrained by hair properties. The method comprises obtaining S10 a database storing data relative to chemical compounds applicable on the class of human hairs.

For each compound the data comprises an identifier, an ingredient, and a performance score of the chemical compound when applied on human hairs. The performance score comprises a manageability score and a goal score.

The method also comprises obtaining S20, from user input, assessed hair properties and hair target properties.

The method also comprises computing S30 at least one goal score and a manageability goal score from the assessed hair properties and hair target properties. The computed at least one goal score and the computed manageability goal score thereby form a signature.

The method also comprises determining S40 at least one identifier of a chemical compound stored in the database corresponding to a chemical compound satisfying the computed at least one goal score and the computed manageability goal score. The satisfying comprises minimizing a distance function between the computed at least one goal score and a corresponding goal score and maximizing a fit-to-manageability function between the computed manageability goal score and the corresponding manageability score.

The method also comprises outputting S50 the determined at least one identifier of the chemical compound to be applied on the human hairs.

The method thus improves the selection of the chemical compound applicable on a class of human hairs as constrained by its hair properties. Indeed, thanks to the computing S30 of the at least one goal score and the manageability goal score from the assessed hair properties and hair target properties, the method obtains an objective indicator for improving the properties of the hair. The method next determines the at least one identifier of a chemical compound stored in the database that corresponds to the chemical compound satisfying the computed at least one goal score and the computed manageability goal score, and hence corresponds to the chemical compound referenced in the database that best improves the properties of the hair upon application of the hair.

In addition, current databases storing data relative to chemical compounds applicable on the class of human hairs may have limited resources. For instance, the database may contain one or more chemical compounds that may relatively improve the properties of the hair but not be an (exact or substantially exact) match for satisfying the computed at least one goal score and the computed manageability goal score. As the satisfying comprises minimizing the distance function and maximizing manageability fit function, the method may still provide the at least one identifier that best improves the properties of the hair based on the available (e.g., limited) data.

The method is computer-implemented. This means that steps (or substantially all the steps) of the method are executed by at least one computer, or any system alike. Thus, steps of the method are performed by the computer, possibly fully automatically, or, semi-automatically. In examples, the triggering of at least some of the steps of the method may be performed through user-computer interaction. The level of user-computer interaction required may depend on the level of automatism foreseen and put in balance with the need to implement user's wishes. In examples, this level may be user-defined and/or pre-defined.

A class of human hairs is a category of human hairs that have one or more hair properties. A hair property may be any chemical or physical characteristic of a human hair such as length, color, texture or feel. The class of human hairs are constrained by hair properties of the class, and thus hairs appertaining to the class may be discerned (e.g., visually or by tact or even chemically) from other hairs of the class by its constraints. For example, a class of human hairs may be a class of straight human hairs, another class may be a class of curly human hairs.

The class may comprise more than one hair property, and may comprise subclasses according to the hair properties. For example, the set of straight human hairs may be decomposed as straight black human hairs and straight blond human hairs. The class may be set in any predetermined manner.

A chemical compound applicable on a class of human hairs is any substance manufactured so as to interact with the hair of the class and/or at least part of the scalp, e.g., modifying properties such as feel, texture, appearance and hygiene.

The chemical compounds applicable on the class of human hairs may comprise one or more of a shampoo, a hair conditioner, a hair oil, a scalp tonic and/or serum. The hair conditioner may be a chemical compound used for improving the manageability, i.e., the feel, texture and/or appearance of the hair of the class. The shampoo may be a chemical compound is used for removing dirt, sebum, sweat, dead skin flakes, etc. from the hair of the class and/or scalp surface using surfactants and/or restore the scalp and/or hair to a clean surface. The scalp tonic may be a chemical compound used for treating the scalp of the human head. The serum may be a chemical compound applicable on the human hair for enhancing scalp health and supporting healthy hair growth, improving hair density, or for treatment of scalp disorders such as dandruff.

By obtaining the database it is meant any kind of processing for retrieving the database. The obtaining may comprise retrieving the database from a non-volatile memory; the database may be obtained from a remote system, e.g., via an internet connection. The obtained database may have been formed at different times, at different locations, with different systems and/or by different persons or entities.

The database stores data relative to chemical compounds applicable on a class of human hairs; the database typically stores data relative to chemical compounds applicable on many classes of human hairs. By "relative" it is meant that the data encodes at least one descriptor of a chemical or physical property of the chemical compound. For each compound, the data comprises an identifier, an ingredient, and a performance score of the chemical compound when applied on human hairs.

The database may have limited resources. That is, the database may comprise significantly lower number of data fields than what would be expected. For example, it may be expected that a database comprises a certain amount of data relative to chemical compounds applicable on the class of human hair (e.g., 10.000 or more chemical compounds). However, a database having limited resources may comprise a significantly lower number of data fields (e.g., 1.000 or less).

By "identifier" it is meant a unique name for discerning the data related to the chemical compound from other data relative to different chemical compounds.

The "ingredient" is data (e.g., a string of characters) describing at least one ingredient contained in the chemical compound.

The "performance score" (a set of values, e.g. numerical values) provides an indicator of the capability of the chemical compound for modifying at least one hair property of a hair of a corresponding class. The performance score comprises a manageability score and a goal score. A manageability score is data (a value, e.g. a numerical value) which denote a capability of at least one of the ingredients of the compound for improving the manageability of the class of human hairs. The goal score is data (a value, e.g. a numerical value) denoting a capability of at least one of the ingredients of the compound for improving a predetermined target goal of the class of human hairs. The predetermined goal may be predetermined in any manner, as a result of an evaluation of the chemical compound, e.g., as obtained from chemical testbeds.

The method obtains S20, from user input, assessed hair properties and hair target properties. By "assessed" it is meant that the hair properties and the hair target properties of human hairs are determined from the user input. In other words, the hair properties are dependent on the data provided from the user. A hair target property may be any desired chemical or physical characteristic of a human hair such as, but not limited to, a desired color, texture or feel.

A user input is any kind of data provided by a user. The user input may thus be fully automated or comprising at least some user interaction. For example, the method may have use different interface peripheric devices for retrieving, manually or at least partially automatically (e.g., fully automatically) the data from the user. The user input may thus comprise one or more of a text input, image input or video input.

For example, a textual input by the user may be compared to a set of predetermined criteria; the method may determine a satisfaction of a hair property (similarly for a hair target property) through a correspondence (e.g., a textual match) between the textual input and one criterion of the set.

The method may obtain the user input S20 through a graphical user interface; The graphical user interface may display user input interface screens. An user input interface screen allows a user to interact with the system. For instance, the user input interface screen may comprise text fields so as to allow the entry of the assessed hair properties and hair target properties by the user in the form of textual information. Additionally or alternatively, the user input interface screen may also display a predetermined set of assessed hair properties and/or hair target properties from which the user may choose to input the assessed hair properties and/or hair target properties. Additionally or alternatively, the user input interface screen may also allow to capture an image from a the user, e.g., an image of the human hair. Additionally or alternatively, the user input interface screen may display one or more icons, each icon mapping a respective user input to a predetermined hair target properties. Additionally or alternatively, the user input interface screen may display one or more images, each image mapping a respective user input to a predetermined hair target properties. The method may perform any kind of data conversion so as to allow the determination of the assessed hair properties and/or hair target properties from the image.

The assessed hair properties and/or the hair target properties may comprise one or more of, but not limited to, a hair type criterion such as straight hair, wavy hair, curly hair or coily hair, a hair length criterion such as short, medium or long hair, a hair condition criterion such as untreated, colored, permed or bleached hair, a hair feel criterion such as healthy or damaged hair, hair tool use criterion, a hair goal criterion such as color protection, repair, shine, smooth, a scalp condition criterion such as oily, dandruff, dry, a scalp goal criterion such as sebum control, anti-dandruff and moisturize, a hair texture criterion, a hair diameter criterion such as fine, medium and coarse, for example in a range between 50 micrometer to 70 micrometer for fine, a range between 70 micrometer to 90 micrometer for medium and a range between 90 micrometer to 120 micrometer for coarse, degree of damage criterion and/or an ethnicity criterion such as Latino, Caucasian, African American and/or Asian.

An assessed hair properties may have a corresponding hair target property. For example, the assessed hair properties may comprise a hair condition criterion, and the assessed hair target properties may comprise also hair condition criterion (also called "hair condition criterion goal" for the sake of distinction).

The assessed hair properties and/or hair target properties may be interrelated with each other. In other words, a hair type criterion may be dependent on another hair type criterion. For instance, the hair diameter criterion may depend on the ethnicity criterion.

The method computes S30 at least one goal score and a manageability goal score from the assessed hair properties and hair target properties.

A goal score is a value (e.g. a numerical value) that determines an extent of satisfaction of the assessed hair property with a respective hair target property (obtained from the user input) or with respect to a predetermined hair target goal. The goal may refer to hair benefits that can be delivered by at least one chemical compound.

For example, the chemical compounds may each have a different degree of hair benefits, e.g., a conditioner may provide a higher degree of conditioning than a shampooing.

In examples, the method may obtain the goal score from the user input S20 through questions displayed through the user input interface. For examples, one question, displayed on a respective user interface may ask for the hair goals of the user; the choices given by the use and its order may be used to determine how well each product in the database fits to that combination of goals. The goal may be predetermined in any manner. For example, a goal may be a hair moisture goal score defined as a degree of satisfaction between the hair condition criterion (comprised in the assessed hair properties) and the hair condition criterion goal (comprised in the assessed hair target properties). For example, a hair target goal may comprise improving the smoothness or color protection of the hair, from which the assessed hair properties are obtained.

A manageability goal score is a value (e.g. a numerical value) that considers the extent of what quantity of conditioning of the hair (from which the assessed hair properties are obtained) is required, based on the assessed hair properties and hair target properties. In other words, the manageability goal score provides an indicator of how the feel, texture and/or appearance of the hair should be improved.

The at least one goal score and the manageability goal score may be computed by the method based on a set of predetermined criteria, such as cleansing, shampooing manageability, conditioner manageability criteria. The criteria may be set in any manner, e.g., as a result from testbed tests. The at least one goal score may comprise one or more of a cleansing score, a cleansing goal score and a treatment score. The manageability goal score may comprise one or more of a goal score of a treatment manageability, a shampoo manageability score and/or a conditioner manageability score.

The computed at least one goal score and the computed manageability score thereby form a signature. By "signature" it is meant that the computed at least one goal and the computed manageability score identify the extent by which the assessed hair properties are representative of the human hair of the class, and the extent by which a predetermined hair target goal is satisfied. The computed at least one goal score and the computed manageability form a signature, i.e. the signature is a value obtained from both the value of the at least one goal score and the value of the manageability score. For example, the computing of the signature may be performed by computing a hash from the values of the at least one goal score and manageability goal score, or obtaining it from a look-up table.

Then, the method determines S40 at least one identifier of a chemical compound stored in the database corresponding to a chemical compound satisfying the computed at least one goal score and the computed manageability goal score. That is, the method traverses the database to retrieve the data relative to at least one chemical compound applicable on the class of the human hairs as determined by the satisfying. The method may perform the determination S40 by any means, e.g., by performing a query comprising the signature to the database.

The satisfying comprises minimizing a distance function between the computed at least one goal score (computed from the assessed hair properties and hair target properties obtained from the user input S20) and a corresponding at least one goal score, comprised in the data relative to a given chemical compound in the database. The distance function may be any mathematical function that takes the computed at least one goal score (from the assessed hair properties and hair target properties) and the corresponding goal score (comprised in the data relative to the chemical compound in the database) as input and outputs a distance between the two scores.

Additionally, the satisfying comprises maximizing a fit-to-manageability function between the computed manageability goal score and the corresponding manageability score. The fit-to-manageability function may be a function that takes the computed manageability goal score and the corresponding manageability score and outputs a fit between the computed manageability goal score and the corresponding manageability score (comprised in the database). In other words, the fit-to-manageability function measures an agreement between the computed manageability goal scores (from the assessed hair properties and hair target properties) and the corresponding manageability score of the compound when traversing the database.

The method outputs S50 the determined at least one identifier of the chemical compound to be applied on the human hairs. The method may perform the outputting S50 through any kind of processing, e.g., setting the at least one identifier in readable format, storing the at least one identifier and/or transmitting the determined at least one identifier to another system.

Thus, the selection of the chemical compound applicable on the class of human hairs is improved. Indeed, a user is provided with an objective indicator (the at least one identifier of the chemical compound) that, when applied to the human hair of the class, results in that the hair of the class is improved according to the goal properties and manageability properties. This objective indicator avoids user bias that may hamper or damage the hair if the chemical compound is chosen incorrectly, e.g., in the case that the user choses a chemical compound not adapted to be applied to the class human hairs.

In addition, the method is able to retrieve an improved selection even when the database having limited resources. Indeed, as the at least one identifier determined at S40 satisfies the computed at least one goal score and the computed manageability goal score, the method leverages from the concomitant information retrieved from the distance function and the fit-to-manageability function for determining the best choice of stored data of the database among the limited data available in the database having limited resources. This is because the method does not rely only on having a closest distance to data relative to a stored chemical compound, but also on the fact that the manageability and target of the stored chemical compound are taken into account to obtain the selection. Hence, should an identifier corresponding to a chemical compound that may be the best choice for the hair of the class is missing, the method is still able to obtain at least one identifier that provides a best approximation so as to obtained the hair target properties when applying the chemical compound on the human hairs of the class. Therefore, the determination on the database is more robust to missing data.

The method may comprise applying the chemical compound on human hairs of a class corresponding to the assessed hair properties the chemical compound identified by the output. By "applying" it is meant that the chemical compound may be put into contact with the human hair of the class. The applying may be performed in any manner by the method, e.g., manually and/or with some degree of automation, e.g., fully automatically. The applying may thereby reach the hair target properties obtained from the user input. Hence, the applying of the chemical compound results in that the hair properties of the class reach the hair target properties, thereby improving the hair properties of the hair.

For example, applying at least a chemical compound comprising a hair conditioner achieves a reduction of friction between strands of hair. Thus, the method allows a smoother brushing or combing of the hair, which might otherwise cause damage to the scalp e.g. through unwanted removal of hair by application of excessive force, or damage to the hair causing hair breakage. Application of conditioner can also improve the properties of hair, such as improvement of hair shine to give a lustrous appearance, improvement of hair strength and resilience to prevent hair breakage, an increase in the retention time of hair color from hair dyes applied to the hair, decreasing the degree of frizz in hair to improve the overall hair appearance.

In another example, applying at least a chemical compound which comprises a shampoo achieves multiple improvements in the hair.

For example, applying a shampoo improves the removal of sebum stemming from sebaceous glands: the sebaceous glands found in the scalp continuously produces sebum, which rises to the scalp surface, spreads onto the scalp and hair. Sebum has a protective and lubricative effect to keratinous materials like skin and hair. However, regular cleansing of the scalp and hair to remove this sebum is also important. The application of shampoo on the hair results in a correct removal of the sebum. Sebum may be oxidized by lipases found on the scalp surface to form lipid peroxides, which has been known to cause hair follicle miniaturization, leading to loss of hair. Excessive sebum on the scalp due to infrequent removal may lead to increased flaking of the scalp due to dandruff. Moreover, the metabolism of sebum by microorganisms found on the scalp may lead to malodor of the hair and scalp. Finally, excessive sebum on the hair due to infrequent removal can lead to hair being excessively weighed down, having a flat and unpresentable appearance, and leading to a loss of perceived volume of hair.

Applying a shampoo on human hairs minimizes problems of infrequent cleansing of hair and scalp such as hair loss, dandruff, malodor, unpleasant appearance of hair.

Shampoos may be formulated with surfactants for cleansing of scalp and hair surface and with hair conditioning agents to deliver a hair benefit such as smoothing of hair surface and thus further improve manageability when applied to the hair of the class.

Shampoos may be formulated to bring about more cleansing effect and less conditioning effect, in order to deliver a perceived hair volume benefit when applied to the hair of the class.

Shampoos may also be formulated to have higher hair manageability during washing, thereby preventing unwanted hair fall due to tangled hair during hair washing, and providing a comfortable and pleasant experience during the cleansing of hair.

Shampoos or conditioners or treatments may also contain chemicals known to penetrate the hair to deliver a strengthening effect to the hair fiber. Free metal ions such as copper are often found in water. These metal ions can interact with hair dye chemicals causing a loss or change of hair color in a person who has colored their hair with hair dye. Shampoos or conditioners or treatments may also contain chemicals that chelate the metal ions and prevent them from interacting with hair dye, therefore keeping the hair dye color for a longer period of time.

Moreover, as the method takes into account the assessed hair properties (and the dependence between the properties), the method ensures that the selected chemical compound is adapted to improve the hair properties of the hair of the class when applying the chemical compound.

In one example, the method may take into account into the dependence between hair diameter criterion and the ethnicity criterion when selecting the at least one chemical compound. Indeed, hair properties depend on ethnicity. Hair diameter may vary depending on the ethnicity. For instance, hair that ranges from about 50 to 70 micrometer in diameter is generally thought of as fine hair, and is typical of Caucasians and African Americans. Additionally, hair that ranges from about 70 to 90 micrometer in diameter is generally thought of as medium hair, and is typical of Asians and Latin Americans. In another example, hair that ranges from about 90 to 120 micrometer in diameter is generally thought of as coarse hair, and is typical of Asians.

In another example, the method may take into account into the dependence between hair diameter criterion and the ethnicity criterion when selecting the at least one chemical compound. Indeed, the hair type may also depend on ethnicity. For instance, hair that is straight can be found in Asians and some Caucasians. Additionally, hair that is wavy can be found in some Asians, Caucasians, and Latin Americans. Hair that is curly (slightly tighter coils) can be found in Latin Americans and some African Americans. Hair that is coily (that is, tight coils) can be found in Latin Americans and some African Americans. Hair that is kinky (that is, very tight coils) can be found in some African Americans.

In another example, the method may take into account the degree of damage of the hair when selecting the at least one chemical compound via the hair damage criterion. Indeed, virgin hair has no damage and the hair surface is relatively smooth. Hair that has been chemically treated by hair dyes has some damage. Hair that has been further treated by heat and chemicals, such as perms, will have even more damage. The degree of damage also corresponds to an increased need for hair conditioning vi. It follows that the degree of conditioning that is needed by hair varies by ethnicities due to the different hair properties.

In other examples, the method may take into account the hair diameter. For examples, a higher conditioning level is generally preferable for Asian hair due to the thicker hair fiber. Conversely, a lower conditioning level is generally preferable for Caucasian hair due to the thinner hair fiber. Hence, the degree of conditioning that is needed by hair depends on the diameter of the hair.

In the case of highly damaged hair either by heat treatments or chemical treatments, the surface of the hair fiber may be rough and worn due to cuticle damage, and have a matte appearance (lack of luster), feel dry due to a lack of moisture. The damaged hair is rough to the touch and is more difficult to manage.

Applying shampoo and/or conditioner of inappropriate manageability level to damaged hair can result in unnecessary loss of hair due to tugging and pulling during the washing process, or during the combing process where hair cannot smoothly detangle from each other, as well as an undesirable hair feel after the hair is dried, whereby the hair may be difficult to manage, difficult to comb through, have a dull appearance, rough texture, or unpleasant feel when touching the hair.

Thus, as the method takes into account the degree of damage of the hair, it is also possible to identify at least one chemical compound that also help to repair, strengthen, improve shine of the hair fiber, to achieve a better overall hair health.

The distance function is further discussed.

The distance function may be a function which is non decreasing as the distance is non-decreasing between the computed at least one goal score and the corresponding goal score (of the at least one identifier of the chemical compound stored in the database). The maximizing function may take the computed at least one goal score and the corresponding goal score as input. The maximizing function may output a decreasing value as the distance between the computed at least one goal score and the corresponding goal score decreases.

The distance may be thus be an absolute value of the difference between the numerical values of the computed at least one goal score and the corresponding goal score, or a square distance. This is only a matter of implementation.

Thus, the distance function allows the method to focus the search on the satisfaction by the corresponding chemical compound of the computed at least one goal score, which is dependent on the assessed hair properties and/or hair target properties. Thus, the method provides the best chemical compound with regards to goal requirements.

When the chemical compounds applicable to human hairs comprise one or more of a shampoo compound, the distance function may comprise a shampoo compound distance term defined by the formula (1):

$$(\text{Cleansing Score}_{Product} - \text{Cleansing Score}_{Target})^2 + (\text{Shampoo Manageability}_{Product} - \text{Shampoo Manageability}_{Target})^2 \quad (1)$$

Cleansing $\text{Score}_{Product}$ is a variable representing a value of a cleansing goal score by the chemical compound. The variable may be an indicator of the degree to which the chemical compound is able to provide a cleansing effect to the scalp and hair. The cleansing score of a chemical compound of a shampoo may be evaluated using tests protocols as known in the art, e.g. dirt dispersion measurement.

Cleansing $\text{Score}_{Target}$ is a variable representing a value of a cleansing goal score computed from the assessed hair properties.

Reference is made to Table I, illustrating an example of user input for the computation of the cleansing goal score.

TABLE I

| Person A-input | Answers | Corresponding Value |
|---|---|---|
| Ethnicity | Caucasian | |
| Manageability Min | | 1 |
| Manageability Max | | 5 |
| Hair Texture | Straight | 1 |
| Hair Condition | Colored | 2 |
| Hair Type | Coarse | 3 |
| Hair Feel | Damaged | 4 |
| Scalp Condition | Oily | |
| Comfort factor | | 0 |
| Cleansing Need | | 1 |

The user may provide, as represented in the leftmost column of Table I, 8 different input requirements for criteria such as ethnicity, hair texture, hair condition, hair type, hair feel, scalp condition, comfort factor and cleansing need. The user may provide different answers for each respective input requirement, e.g., in the form of textual input such as "Caucasian" for ethnicity. The method may map each provided answer to a corresponding value. In this example, an ethnicity may also comprise manageability thresholds which set a maximum and minimum values Manageability Min and Manageability Max.

The method may obtain the manageability thresholds from a manageability look-up table. Table II below illustrates an example of the manageability look-up table for two different ethnicities: Caucasian and Asian.

TABLE II

| Ethnicity | Shampoo Manageability Min | Shampoo Manageability Max |
|---|---|---|
| Caucasian | 1 | 5 |
| Asian | 2 | 4 |

The method may map each provided answer to the corresponding value from a look-up table for each answer/input. Table III below illustrates a look-up table for the scalp condition.

TABLE III

| Scalp Condition | Comfort Factor | Cleansing Need |
|---|---|---|
| Normal | 0 | 0 |
| Oily | 0 | 1 |

The Cleansing $\text{Score}_{Target}$ may be computed from the formula.

$$\text{Cleansing Score}_{Target} = 4 + \text{Comfort Factor} + \text{Cleansing Need} = 4 - 0 + 1 = 5$$

Shampoo $\text{Manageability}_{Product}$ is a variable representing a value of a goal score of a shampooing manageability by the chemical compound. The variable may be an indicator of the degree to which the chemical compound is able to provide a hair manageability benefit to the scalp and hair. The variable Shampoo $\text{Manageability}_{Product}$ is typically obtained as the result of tests as known in the art, e.g. texture analysis of hairs.

Shampoo $\text{Manageability}_{Target}$ is a variable representing a value of a shampoo manageability goal score computed from the assessed hair properties and hair target properties.

Table IV below illustrates a user input for the computation of the value of the shampoo manageability goal score.

TABLE IV

| Person A | Answers | Corresponding Value |
|---|---|---|
| Ethnicity | Caucasian | 1 |
| Shampoo Manageability Min | | 1 |
| Shampoo Manageability Max | | 5 |
| Hair Texture | Straight | 1 |
| Hair Condition | Colored | 2 |
| Hair Type | Coarse | 3 |
| Hair Feel | Damaged | 4 |

For each ethnicity, the method may obtain a shampoo manageability minimum and maximum values, e.g., from a look-up table. Table V shows an example of look up table for shampoo manageability.

TABLE V

| Ethnicity | Shampoo Manageability Min | Shampoo Manageability Max |
|---|---|---|
| Caucasian | 1 | 5 |
| Asian | 2 | 4 |

The variable Shampoo $\text{Manageability}_{Target}$ may thus be computed, based on the input, according to a formula of the type:

$$\text{Shampoo Manageability}_{Target} = \text{Shampoo Manageability}_{Min} + (\text{Shampoo Manageability}_{Max} - \text{Shampoo Manageability}_{Min}) \times \frac{\text{Hair Texture} + \text{Hair Condition} + \text{Hair Type} + \text{Hair Feel}}{\text{Max value of (Hair Texture} + \text{Hair Condition} + \text{Hair Type} + \text{Hair Feel)}} = 1 + (5-1) \times \frac{1+2+3+4}{20} = 1 + 4 \times \frac{10}{20} = 1 + 2 + 3.$$

Wherein the variable Max value is computed from the four variables in the argument times five, which is a maximum value of the variables. When the chemical compounds applicable to human hairs comprise one or more of a hair conditioner compounds, the distance function may comprise a hair conditioner compound distance term defined by the formula (2):

$$\text{Conditioner Manageability}_{Target} - \text{Cleansing Score}_{Target} \tag{2}$$

Conditioner $\text{Manageability}_{Target}$ is a variable representing a value of a conditioner manageability goal score computed from the assessed hair properties and hair target properties. The variable may be an indicator of the degree to which the chemical compound is able to provide a hair manageability benefit to the hair.

Table VI below illustrates a user input for the computation of the value of the conditioner manageability goal score.

TABLE VI

| Person A | Answers | Corresponding Value |
|---|---|---|
| Ethnicity | Caucasian | |
| Conditioner Manageability Min | | 1 |
| Conditioner Manageability Max | | 5 |
| Hair Texture | Straight | 1 |
| Hair Condition | Colored | 2 |
| Hair Type | Coarse | 3 |
| Hair Feel | Damaged | 4 |
| Hair Tools | Straightener | 5 |
| Hair Length | Long | 5 |
| Hair Goal 1 | Smooth | |
| Hair Goal 2 | Color Protection | |
| Hair Goal 3 | Shine | |
| Volume Modifier | | 0 |
| Conditioning Modifier | | 5 |
| MRS Check | | 0 |

For each ethnicity, the method may obtain a conditioner manageability minimum and maximum values, e.g., from a look-up table. Table VII shows an example of look up table for conditioner manageability.

TABLE VII

| Ethnicity | Conditioner Manageability Min | Conditioner Manageability Max |
|---|---|---|
| Caucasian | 1 | 5 |
| Asian | 2 | 7 |

The method may thus compute the following formulae, from the values in table VI:

$$\text{Hair Factor} = \text{Hair Texture} + \text{Hair Condition} + \text{Hair Type} + \text{Hair Feel} + \text{Hair Tools} + \text{Hair Length} + \text{Volume Modifier} + \text{Conditioning Modifier} = 1+2+3+4+5+5+0+5=25$$

$$\text{Cleansing Score}_{Target} = \text{Conditioner Manageability}_{Min} + (\text{Conditioner Manageability}_{Max} - \text{Conditioner Manageability}_{Min}) \times \frac{\text{Hair Factor}}{\text{Max value of Hair Factor}} + MRS\text{ Check} = 1+(5-1)\times\frac{25}{35}+0 = 1+4\times\frac{5}{7} \cong 4$$

When the chemical compounds applicable to human hairs comprise one or more of a hair treatment compound, the distance function may comprise a hair treatment compound distance term defined by the formula (3):

$$\text{Treatment Manageability}_{Product} - \text{Treatment Score}_{Target} \quad (3)$$

Treatment Manageability$_{Product}$ is a variable representing a value of a goal score of a treatment manageability by the chemical compound. The variable may be an indicator of the degree to which the chemical compound is able to provide a hair manageability benefit to the hair.

Treatment Score$_{Target}$ is a variable representing a value of a treatment goal score computed from the assessed hair properties and hair target properties.

Table VIII below illustrates a user input for the computation of the value of the treatment goal score.

TABLE VIII

| Person A | Answers | Corresponding Value |
|---|---|---|
| Ethnicity | Caucasian | 1 |
| Treatment Manageability Min | | 2 |
| Treatment Manageability Max | | 7 |
| Hair Texture | Straight | 1 |
| Hair Condition | Colored | 2 |
| Hair Type | Coarse | 3 |
| Hair Feel | Damaged | 4 |
| Hair Tools | Straightener | 5 |
| Hair Length | Long | 5 |
| Hair Goal 1 | Smooth | |
| Hair Goal 2 | Color Protection | |
| Hair Goal 3 | Shine | |
| Volume Modifier | | 0 |
| Conditioning Modifier | | 5 |
| MRS Check | | 0 |

For each ethnicity, the method may obtain a treatment manageability minimum and maximum values, e.g., from a look-up table. Table IX shows an example of look up table for treatment manageability for ethnicity Caucasian and Asian.

TABLE IX

| Ethnicity | Treatment Manageability Min | Treatment Manageability Max |
|---|---|---|
| Caucasian | 2 | 7 |
| Asian | 3 | 8 |

The method may thus compute the following formulae, from the values in Table VIII:

$$\text{Hair Factor} = \text{Hair Texture} + \text{Hair Condition} + \text{Hair Type} + \text{Hair Feel} + \text{Hair Tools} + \text{Hair Length} + \text{Volume Modifier} + \text{Conditioning Modifier} = 1+2+3+4+5+5+0+5=25$$

$$\text{Treatment Score}_{Target} = \text{Treatment Manageability}_{Min} + (\text{Treatment Manageability}_{Max} - \text{Treatment Manageability}_{Min}) \times \frac{\text{Hair Factor}}{\text{Max value of Hair Factor}} + MRS\text{ Check} = 2+(7-2)\times\frac{25}{35}+0 = 2+5\times\frac{5}{7} \cong 6$$

In these examples, the distance function calculates the distance between a target and each for the chemical compounds of the product found in the product database, e.g. for shampoos, conditioners and treatments. The distance function does not have weights but the functions to determine fit scores and average score has weights.

The method thus takes into account the concomitant information of different goals so as to find a product that satisfies a goal on cleansing, shampooing manageability, treatment manageability, cleansing goal, treatment goal, shampoo manageability goal score, and conditioner manageability goal score so as to provide a correct mixture of a chemical compound comprising the shampoo compound and the hair conditioner compound.

In an example, the chemical compounds applicable to human hairs comprise one or more of a shampoo compound and a hair conditioner compound. The distance function comprises the shampoo compound distance term defined by the formula (1) computed for each shampoo compound and the distance function comprises a hair conditioner compound distance term defined by the formula (2) for each conditioner compound.

In another example, if the chemical compounds applicable to human hairs comprise one or more of a shampoo compound, a hair conditioner compound, and a treatment compound, the distance function comprises the shampoo compound distance term defined by the formula (1) computed for each shampoo compound, the distance function comprises a hair conditioner compound distance term defined by the formula (2) for each conditioner compound, and the distance function comprises a treatment compound distance term defined by the formula (3) for each treatment compound.

The fit-to-manageability function is further discussed.

The fit-to-manageability function may be a function Fit (Manageability) for in which its parameters may be varied so that a computed manageability fits the corresponding manageability score of the product stored in the database. The fit-to-manageability function may be defined by the following formula (4):

to the fit-to-manageability function, the method may focus the determination of the at least one identifier of a chemical compound stored in the database with respect to the manageability score of the product stored in the database. This is because, by construction, the fit-to-manageability function comprises a single greatest value), and thus allows a sharp determination of the chemical compound with respect to its satisfaction of the manageability goal score computed from the assessed hair properties and/or hair target properties. Hence, the at least one identifier of the chemical compound determined by the method has an additional degree of freedom when traversing the database (instead of just minimizing the distance function) and thus the method may output at least one identifier of the chemical compound corresponding to the chemical compound that improves the manageability of the hair of the class when applied.

The outputting S50 of the determined at least one identifier of the chemical compound may comprise averaging the computed at least one goal score and the computed manageability goal score. In other words, the output may determine a value (called "average") which consists of the mean value of the computed at least one goal score and the computed manageability goal score. The at least one identifier of the chemical compound may be ranked according a $$\text{Fit (Manageability)} = \begin{cases} \left(\dfrac{\text{Manageability}_{Product} - LSL}{\text{Manageability Score} - LSL}\right)^{LP}, & \text{Manageability}_{Product} \le \text{Manageability Score} \\ \left(\dfrac{USL - \text{Manageability}_{Product}}{USL - \text{Manageability Score}}\right)^{UP}, & \text{Manageability}_{Product} > \text{Manageability Score} \end{cases} \tag{4}$$

wherein:

Manageability is a vector (e.g., multidimensional, at least two-dimensional) comprising $\text{Manageability}_{Product}$ variable and a Manageability Score variable, where $\text{Manageability}_{Product}$ is a variable representing a value of a manageability score by the chemical compound and a Manageability Score is a variable representing a value of a manageability goal score computed from the assessed hair properties and hair target properties.

LSL is a first variable and USL is a second variable.

LP is a lower exponent variable depending on user input and UP is an upper exponent variable depending on user input.

The first variable and the second variable may be a lower specification limit and upper specification limit respectively. The lower specification limit and upper specification limit are used for a normalization of the fit.

The LP exponent may define a gradient of the fit-to-manageability function when the value of the manageability score by the chemical compound is less or equal than the value of the manageability goal score computed from the assessed hair properties and hair target properties. The UP exponent may define a gradient of the fit-to-manageability function when the value of the manageability score by the chemical compound is greater than the value of the manageability goal score computed from the assessed hair properties and hair target properties. Thus, the fit-to-manageability function outputs a value corresponding to a summit (i.e., the greatest value of the fit-to-manageability function) when the value of the manageability score by the chemical compound is less or equal than the value of the manageability goal score computed from the assessed hair properties and/or hair target properties.

This results in an improved selection of the chemical compound when the database has limited resources. Thanks fit-to-goal distance to the average. In other words, the method may measure a distance (i.e., the fit-to-goal distance) between the goal score of the at least one identifier of the at least one chemical compound to the average, and rank the at least one chemical compound according to the fit-to-goal distance. By convention, a determined chemical compound may be ranked increasingly as the fit-to-goal distance to the average. For example, the determined chemical compound having the shortest fit-to-goal distance to the average may be ranked as "1", and the rank of other determined identifier of chemical compounds may be increased according to its distance, e.g., "2" and "3" for the second closest and the third closest determined identifiers of the chemical compound (from the at least one chemical compound), and so on.

Therefore, the output by the method provides a selection which is objectively guiding the user for selecting a chemical compound to be applied on the class of human hairs according to its relevance with respect to a given goal. This yet improves the selection of the at least one chemical compound.

The fit-to-goal function may be defined by the following equation (5):

$$\text{Fit to goal} = \sum \text{Weight}_i \times \text{Goal}_i \tag{5}$$

where $$\text{Goal}_i = \begin{cases} 0, & \text{Goal Value}_{Product} \le LSL \\ \dfrac{\text{Goal Value}_{Product}}{\text{Goal Threshold}_i}, & LSL < \text{Goal Value}_{Product} < \text{Goal Threshold}_i \\ 1, & \text{Goal Value}_{Product} \ge \text{Goal Threshold}_i \end{cases}$$

$Goal_i$ is a value representing a computed at least one goal score.

Goal $Value_{Product}$ is a variable representing a value of the performance score corresponding to the corresponding identifier of the chemical compound stored in the database. The variable may also encode a set of values for the chemical compound, the set of values comprising the shampoo manageability, cleansing score, conditioner manageability, treatment manageability, and goal values for each product that indicates the ability of the product to deliver a particular hair benefit.

$GoalThreshold_i$ is a variable representing a value of a goal priority. The value is a non-negative number varying between 0 to 1. The value of the goal priority may be predetermined in any manner, e.g. the values of goal priorities may be stored in the database.

$Weight_i$ is a predetermined weight, i.e., a non-negative number, e.g., between 0 and 1.

The predetermined weight may be predetermined from the user input S20. The value of the predetermined weight may be affected by the order of the choice and number of the goals that are affected by the fit calculation, e.g. if there is only 1 goal that needs to be factored for the fit, the predetermined weight may be set as 1 (that is, the highest value possible. If there are 2 goals then the weight may be set for example 0.7 for the $1^{st}$ goal, and 0.3 for the $2^{nd}$ goal, so that the total sum results to 1. In another examples, if there are 3 goals then the predetermined weight may have values such as 0.5, 0.3, 0.2 for a $1^{st}$, 2nd and 3rd goal respectively. By convention, the relative weights may be set such that a first weight is greater than a second weight and to a third weight respectively, e.g., $1^{st}$ weight>$2^{nd}$ weight>$3^{rd}$ weight.

The specific function thus modifies the weights of each computed at least one goal score, and thus the method may create different priorities when determining the ranking, with respect to the weighted goals. This further improves the objective selection of the chemical compound according to the different priorities; for instance two chemical compounds may cause a same effect (a goal) on the hairs, but the chemical compound with the simplest application (e.g. less application time on the hair) can be prioritized.

Outputting S50 the determined at least one identifier of the chemical compound further may comprise displaying the at least one identifier of the chemical compound on a display engine. A display engine may be any processing unit in the computer adapted for generating a video signal in a display device. Hence, by "displaying" it is meant that the method may send instructions, interpretable by the display engine, such that the at least one identifier of the chemical compound may be shown in the display device.

The method may also perform any kind of data conversion so that the at least one identifier of the chemical compound may be readable by a human person.

This further improves the selection of the chemical compound applicable on the class of human hairs, as the method presents an objective indicator for performing such selection. This ensures that the application is objectively realized.

A typical example of computer-implementation of a method is to perform the method with a system adapted for this purpose. The system may comprise a processor coupled to a memory and a display device, the memory having recorded thereon a computer program comprising instructions for performing the method. The memory may also store the database storing data relative to chemical compounds applicable on the class of human hairs. The memory is any hardware adapted for such storage, possibly comprising several physical distinct parts (e.g. one for the program, and possibly one for the database).

The processor may operate with the display device to display the set of input interface screens.

For each displayed input interface screens, the processor may input by the user a value setting at least one hair property or hair target property. The input interface screens may be presented in any manner, e.g., sequentially (such as in the form of a questionnaire). The processor may also display the outputted at least one identifier of the chemical compound to be applied on the human hairs.

Figure 2:
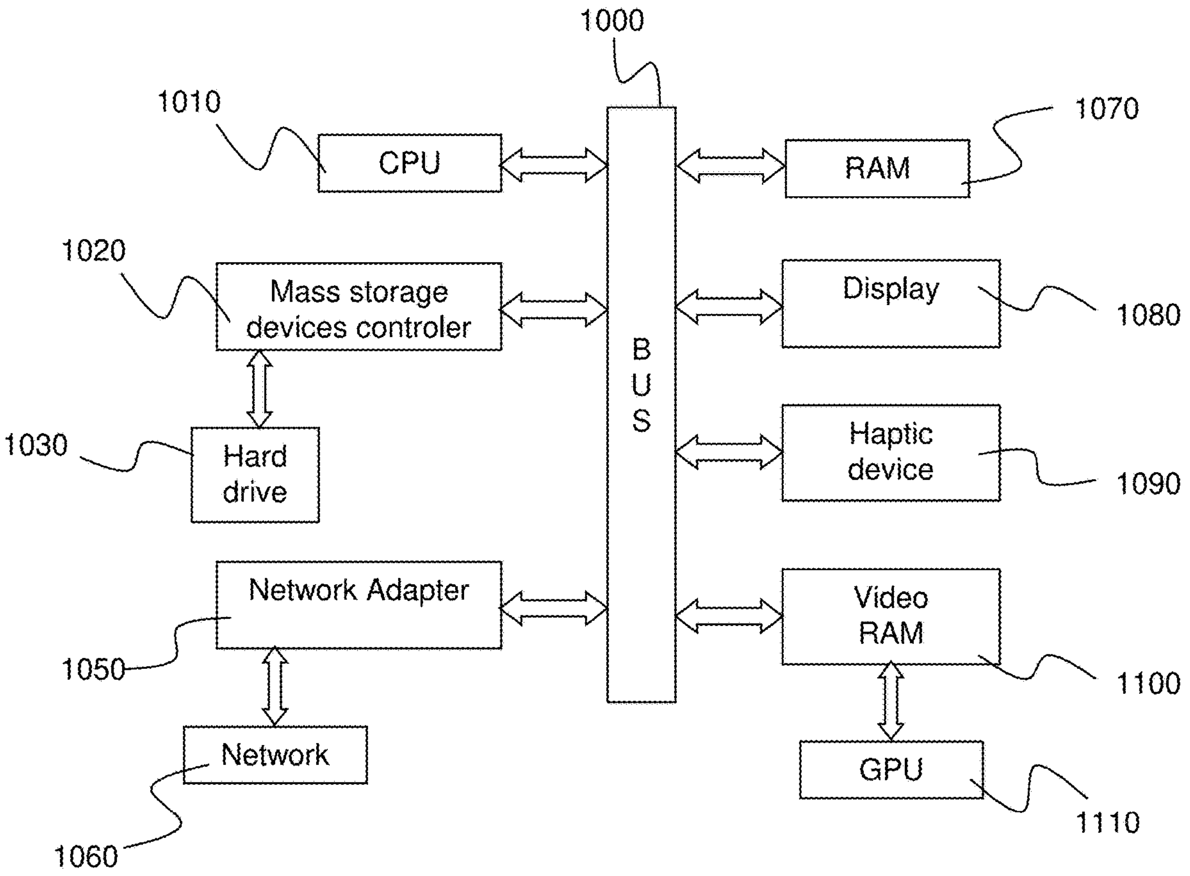
FIG. 2 shows an example of the system.

FIG. 2 shows an example of the system, wherein the system is a client computer system.

The client computer of the example comprises a central processing unit (CPU) 1010 connected to an internal communication BUS 1000, a random access memory (RAM) 1070 also connected to the BUS. The client computer is further provided with a graphical processing unit (GPU) 1110 which is associated with a video random access memory 1100 connected to the BUS. Video RAM 1100 is also known in the art as frame buffer. A mass storage device controller 1020 manages accesses to a mass memory device, such as hard drive 1030. Mass memory devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks. Any of the foregoing may be supplemented by, or incorporated in, specially designed ASICs (application-specific integrated circuits). A network adapter 1050 manages accesses to a network 1060. The client computer may also include a haptic device 1090 such as cursor control device, a keyboard or the like. A cursor control device is used in the client computer to permit the user to selectively position a cursor at any desired location on display 1080. In addition, the cursor control device allows the user to select various commands, and input control signals. The cursor control device includes a number of signal generation devices for input control signals to system. Typically, a cursor control device may be a mouse, the button of the mouse being used to generate the signals. Alternatively or additionally, the client computer system may comprise a sensitive pad, and/or a sensitive screen.

The computer program may comprise instructions executable by a computer, the instructions comprising means for causing the above system to perform the method. The program may be recordable on any data storage medium, including the memory of the system. The program may for example be implemented in digital electronic circuitry, or in computer hardware, firmware, software, or in combinations of them. The program may be implemented as an apparatus, for example a product tangibly embodied in a machine-readable storage device for execution by a programmable processor. Method steps may be performed by a programmable processor executing a program of instructions to perform functions of the method by operating on input data and generating output. The processor may thus be programmable and coupled to receive data and instructions from, and to transmit data and instructions to, a data storage system, at least one input device, and at least one output device. The application program may be implemented in a high-level procedural or object-oriented programming language, or in assembly or machine language if desired. In any case, the language may be a compiled or interpreted language. The program may be a full installation program or an update program. Application of the program on the system results in any case in instructions for performing the method. The computer program may alternatively be stored and executed on a server of a cloud computing environment, the server being in communication across a network with one or more clients. In such a case a processing unit executes the instructions comprised by the program, thereby causing the method to be performed on the cloud computing environment.

The system may further comprise a camera. The camera may be configured to capture an image of a user's human hair. The processing unit may be further configured to assess, from the captured image, the hair properties.

Optionally, a handheld hair and scalp measurement device can be used to capture and record readings from the physical hair and scalp to directly input into questionnaire for product recommendation.

The system may thus be used to take a high magnification image of the hair fibers and scalp to determine, hair thickness, density, and hair cuticle condition and scalp conditions to match with pre-coded reference data ranges to directly input into user questionnaire app for higher accuracy results.

The system may communicate to a centralized system and its data fed into the a reference data base for output into the respective questionnaire answers (e.g. fine, medium coarse hair), now based on captured data.

The method may also incorporate a machine learning component. The machine-learning component may be trained on a database of user feedback of chemical compounds. The user feedback may comprise a rating on a defined scale regarding the extent to which the product recommended was able to effectively provide hair manageability, and the extent to which the product recommended was able to effectively deliver on the selected goals. The machine-learning component may be configured to improve the recommendation algorithm by adjusting variables within the method.

Examples of the method are discussed with reference to FIGS. 3 to 9.

The method presents nine input interface screens. Each input interface screen displays a question and also displays a text field to collect the respective answer as user input. Typical questionnaires may have a database or table containing a list of all available products, with corresponding values for each question-answer combination. The answers provided by the user through the input collection process is matched to the database, and the corresponding relevant values selected and added together, with the usage of weights where needed.

In this tested implementation, the questions are used to collect hair properties for objectively determining how much conditioning the hair needs. The respective answers are assigned a number which increases with the degree of which conditioning is needed as a conditioning need target property.

Reference is made to Table X, illustrating the variables that are used for assigning and calculating values according to the user input.

TABLE X

| Input Variables | Options | Definitions |
|---|---|---|
| Ethnicity ID | Asian/Caucasian/African American/Latin American | Ethnicity ID is an ID number that defines a set of values that code for ethnic differences in manageability |
| Hair Length | Short/Medium/Long | Hair Length is a value that codes for the length of hair and degree corresponds to the need for manageability |
| Hair Texture | Straight/Wavy/Curly/Coiled | Hair Texture is a value that defines the texture of the hair and corresponds to the need for manageability which increases with the degree of change in texture |
| Hair Condition | Natural/Permanent Colored/Lightened Colored/Permed/Chemically Straightened | Hair condition is a value that defines the state of the hair condition and corresponds to the need for manageability, which increases as the hair damage increases |
| Hair Type | Fine/Medium/Coarse | Hair type is a value that defines the diameter of the individual hair fiber, and corresponds to the need for manageability |
| Hair Feel | Healthy/Dry and Frizzy/Damaged | Hair feel is a value that defines the current state of the hair, how it feels, and corresponds to the degree of hair conditioning required. |

TABLE X-continued

| Input Variables | Options | Definitions |
|---|---|---|
| | | Damaged hair requires more conditioning than healthy hair, and dry and frizzy hair requires more conditioning than Healthy hair. |
| Hair Tool | Hair Dryer/Straightener/Curler/None | Hair tools is a value that defines the extent to which heat damage is administered to the hair fiber. A strong heat tool usually corresponds to higher damage hair which needs more manageability |
| Scalp Condition | Normal/Oily/Dry/Sensitive/Dandruff | Scalp condition defines the state of the scalp and degree to which greater or lesser or normal cleansing amount is needed, corresponding to the oiliness or dryness of the scalp condition |
| Hair Goal 1/2/3 | Smooth and Sleek, Color Protection, More Shine, More Volume, More Moisture, More Strengthened, More repaired, Fuller Thicker, Protect Hair, Curl Definition | Goal values define the various aspects or attributes of hair which the user would like to obtain. The order in which the goals are selected indicates the relative importance of the goals. |
| Comfort Factor | Depends on Scalp condition answer | Comfort factor is a value that depends on the answer of scalp condition, it indicates whether a scalp requires less cleansing |
| Cleansing Need | Depends on Scalp condition answer | Cleansing need is a value that depends on the answer of scalp condition. It indicates whether a scalp requires more cleansing |
| Cleansing Score | Baseline cleansing value + Comfort Factor + Cleansing Need | Cleansing score is an overall score representing the cleansing target score of the user. |
| Shampoo Manageability Min | Depends on Ethnicity ID | Shampoo manageability min represents the minimum shampoo manageability value for a particular ethnicity ID value, |

TABLE X-continued

| Input Variables | Options | Definitions |
|---|---|---|
| | | as the degree of manageability varies with the hair type found in each ethnicity |
| Shampoo Manageability Max | Depends on Ethnicity ID | Shampoo manageability max represents the maximum shampoo manageability value for a particular ethnicity ID value, as the degree of manageability varies with the hair type found in each ethnicity |
| Shampoo manageability Delta | Shampoo Manageability Max − Shampoo Manageability Min | Shampoo manageability delta represents the difference between the maximum and minimum values of shampoo manageability |
| Total Shampoo Manageability | Hair Feel + Hair Type + Hair Condition + Hair Texture | Total Shampoo manageability is the sum of all hair factors that contribute to the manageability need in a shampoo. |
| Max of Total Shampoo Manageability | This is the maximum value of Total Shampoo Manageability which is the sum of the maximum values of Hair Feel, hair Type, Hair Condition and Hair Texture, and this value is a constant | |
| Shampoo Manageability $\text{Score}_{Target}$ | $= \text{Shampoo Manageability}_{Min} + \text{Shampoo manageability}_{Delta} \times \frac{\text{Total Shampoo Manageability}}{\text{Max of Total Shampoo Manageability}}$ | Shampoo Manageability $\text{Score}_{Target}$ is a variable representing the value of a shampoo manageability goal score computed from the assessed hair properties and hair target properties |
| Conditioning Need | = Hair Type + Hair Length + Hair Condition + Hair Feel + Hair Tool + Hair Texture | Conditioning need is a value that represents the sum of all factors that contribute to the manageability need for the user's hair |
| Volume Modifier | Depends on volume goal | Volume modifier is a value that depends on whether a volume goal is chosen, and if chosen, assumes a negative value |

TABLE X-continued

| Input Variables | Options | Definitions |
|---|---|---|
| | | to reduce the hair factor |
| Conditioning Modifier | Depends on goal selected | Conditioning modifier is a value that depends on whether a goal related to conditioning requirement is chosen, and if chosen, assumes a positive value to increase the hair factor |
| Hair Factor (HF) | = Conditioning Need + Conditioning Modifier + Volume modifier<br>And Hair Factor $(HF) = \begin{cases} 0, & HF \leq 0 \\ HF. & \text{otherwise} \end{cases}$ | Hair Factor is the sum of the conditioning need, volume modifier and conditioning modifiers and represents the total conditioning need of the hair combined with the ideal state of the user. |
| Maximum of Hair Factor | This is the maximum value of Hair Factor which is the sum of the maximum values of Hair Feel, Hair Type, Hair Condition and Hair Texture, Hair Tool, Hair Texture, Volume modifier and Conditioning Modifier and this value is a constant | |
| MRS Check | Depends on goals selected | MRS check is a variable that depends on whether a particular goal is chosen, and if chosen, modifies the Conditioner and Treatment score to account for a higher desired conditioning effect based on the selected goals |
| Conditioner Manageability Min ($CM_{Min}$) | Depends on Ethnicity ID | Conditioner Manageability Min is a value that depends on the Ethnicity ID and represents the minimum manageability value that a particular ethnicity should receive for a conditioner, based on properties of hair that are typically found in a particular ethnicity |
| Conditioner Manageability Max ($CM_{Max}$) | Depends on Ethnicity ID | Conditioner Manageability Max is a value that depends on the Ethnicity ID and represents the maximum manageability value that a particular |

TABLE X-continued

| Input Variables | Options | Definitions |
| --- | --- | --- |
| | | ethnicity should receive for a conditioner, based on properties of hair that are typically found in a particular ethnicity |
| Conditioner Manageability Delta | Conditioner Manageability Max − Conditioner Manageability Min | Conditioner Manageability Delta is a value that represents the difference between the Maximum and Minimum manageability for a conditioner for a particular ethnicity |
| Treatment Manageability Min ($TM_{min}$) | Depends on Ethnicity ID | Treatment Manageability Min is a value that depends on the Ethnicity ID and represents the minimum manageability value that a particular ethnicity should receive for a treatment, based on properties of hair that are typically found in a particular ethnicity |
| Treatment Manageability Max ($TM_{max}$) | Depends on Ethnicity ID | Treatment Manageability Max is a value that depends on the Ethnicity ID and represents the maximum manageability value that a particular ethnicity should receive for a treatment, based on properties of hair that are typically found in a particular ethnicity |
| Treatment Manageability Delta | Treatment Manageability Max − Treatment Manageability Min | Treatment Manageability Delta is a value that represents the difference between the Maximum and Minimum manageability for a treatment for a particular ethnicity |

TABLE X-continued

| Input Variables | Options | Definitions |
| --- | --- | --- |
| Conditioner Manageability Score (CMS) | $= \text{Conditioner Min} + \text{Conditioner Delta} \times \frac{\text{Hair Factor}}{\text{Maximum of Hair Factor}} + MRS\ \text{Check}$ <br> And conditioner manageability score $(CMS) = CMS = \begin{cases} CM_{Min}, & CMS \le CM_{Min} \\ CMS, & CM_{Min} < CMS < CM_{Max} \\ CM_{Max}, & CMS \ge CM_{Max} \end{cases}$ | Conditioner Manageability Score is a score that defines the target manageability score that a particular profile should receive for a treatment product, based on the user inputs such as hair properties and desired hair outcomes |
| Treatment Manageability Score (TMS) | $= \text{Treatment Min} + \text{Treatment Delta} \times \frac{\text{Hair Factor}}{\text{Maximum of Hair Factor}} + MRS\ \text{Check}$ <br> And treatment manageability score $(TMS) = \begin{cases} TM_{Min}, & TMS \le TM_{Min} \\ TMS, & TM_{Min} < TMS < TM_{Max} \\ TM_{Max}, & TMS \ge TM_{Max} \end{cases}$ | Treatment Manageability Score is a score that defines the target manageability score that a particular profile should receive for a treatment product, based on the user inputs such as hair properties and desired hair outcomes |

In a tested implementation, the assessed hair properties obtained as a result of the user input are encoded in the variables: Hair Type, Hair Length, Hair Condition, Hair Condition, Hair Feel, Hair Texture and Hair Tools.

The mathematical formula for calculating the degree of which conditioning is needed is given by:

$$\text{Conditioning Need} = \text{Hair Type} + \text{Hair Length} + \text{Hair Condition} + \text{Hair Feel} + \text{Hair Texture} + \text{Hair Tools};$$

The conditioning need is used for calculating other scores. A hair factor goal score is calculated as:

$$\text{Hair Factor} = \begin{cases} 0 \text{ if Conditioning Need} + \text{Conditioning Modifier} + \text{Volume Modifier} = 0 \\ \text{Conditioning Need} + \text{Conditioning Modifier} + \text{Volume Modifier otherwise} \end{cases}$$

where Conditioning Modifier and Volume Modifier depends on whether certain hair goals are selected.

Other mathematical formula that are used by the method for computing goal scores and manageability goal scores are:

$$\text{Conditioner Delta} = \text{Conditioner Max} - \text{Conditioner Min}$$

$$\text{Treatment Delta} = \text{Treatment Max} - \text{Treatment Min};$$

where Conditioner Min, Conditioner Max, Treatment Min, Treatment Max assume different values depending on the ethnicity (which is entered by the user in an interface screen).

An MRS Check and a conditioner score are also computed as follows:

$$MRS\ \text{Check} = \begin{cases} 1 \text{ if Moisture, Repair, or Smooth goal selected} \\ 0 \text{ otherwise} \end{cases}$$

-continued $$\text{Conditioner Score} = \text{Conditioner Min} + \text{Conditioner Delta} * \left(\frac{\text{Hair Factor}}{30}\right) + MRS\ \text{check}$$

The MRS Check is subject to the constraint:

$$\text{Conditioner Score} = \begin{cases} \text{Conditioner Max if Conditioner Score} > \text{Conditioning Max} \\ \text{Conditioner Score otherwise} \end{cases}$$

A treatment goal score is computed as follows:

$$\text{Treatment score} = \text{Treatment Min} + \text{Treatment Delta} * \left(\frac{\text{Hair Factor}}{30}\right) + MRS \text{ check}$$

*a*. Subject to the below constraint $$b.\ \text{Treatment Score} = \begin{cases} \text{Treatment Max if Treatment Score} > \text{Treatment Max} \\ \text{Treatment Score otherwise} \end{cases}$$

The method may also display another set of input interface screens each comprising questions are used to understand the state of the scalp of the user.

The following formula is used to calculate the cleaning goal score:

$$\text{Comfort Factor} = \begin{cases} 1 \text{ if Scalp Condition} = \text{Dry or Sensitive} \\ 0 \text{ Otherwise} \end{cases}$$

$$\text{Cleansing Need} = \begin{cases} 1 \text{ if Scalp Condition} = \text{Oily} \\ 0 \text{ Otherwise} \end{cases}$$

$$\text{Cleansing Score} = 4 + \text{Comfort Factor} + \text{Cleansing Need}.$$

data relative to the chemical compounds. This can be done for Shampoos, Conditioners and Treatments. The distance function does not have weights.

For the shampoo, the distance comprises a term of the type:

$$(\text{Cleansing Score}_{Product} - \text{Cleansing Score}_{Target})^2 +$$

$$(\text{Shampoo Manageability}_{Product} - \text{Shampoo } ManageabilityScore_{Target})^2$$

For the conditioner, the distance comprises a term of the type:

$\text{Conditioner Manageability}_{Product}$–$\text{Conditioner Score}_{Target}$ For the treatment, the distance comprises a term of the type:

$\text{Treatment Manageability}_{Product}$–$\text{Treatment Score}_{Target}$

The fit-to-manageability function is now further discussed.

$$\text{Fit (Manageability)} = \begin{cases} \left(\frac{\text{Manageability}_{Product} - LSL}{\text{Manageability Score} - LSL}\right)^{LP}, & \text{Manageability}_{Product} \leq \text{Manageability Score} \\ \left(\frac{USL - \text{Manageability}_{Product}}{USL - \text{Manageability Score}}\right)^{UP}, & \text{Manageability}_{Product} > \text{Manageability Score} \end{cases}.$$

The method also computes a shampoo manageability score via the formula:

$$\text{Shampoo Manageability} = \text{Hair Feel} + \text{Hair Type} + \text{Hair Condition} + \text{Hair Texture}$$

$$\text{Shampoo Manageability Score} = A + B * \frac{\text{Shampoo } Manageabiity}{20}.$$

Where A and B take different values depending on ethnicity.

The final shampoo score is made of the cleansing score and the shampoo manageability score.

The method may additionally display another set of input interface screens to retrieve user inputs to allow the method to understand the ideal condition of the user's hair or desired hair target properties of what the user wants to achieve after finding the right chemical compound. The user inputs obtained from these input interface screens are assigned a letter code which indicates the performance goals that they want to have from the product.

FIG. 3 illustrates a table 300 comprising goal scores for several chemical compounds. A chemical compound 310 comprises seven chemical scores 320-380.

The distance function is further discussed.

Figure 4:
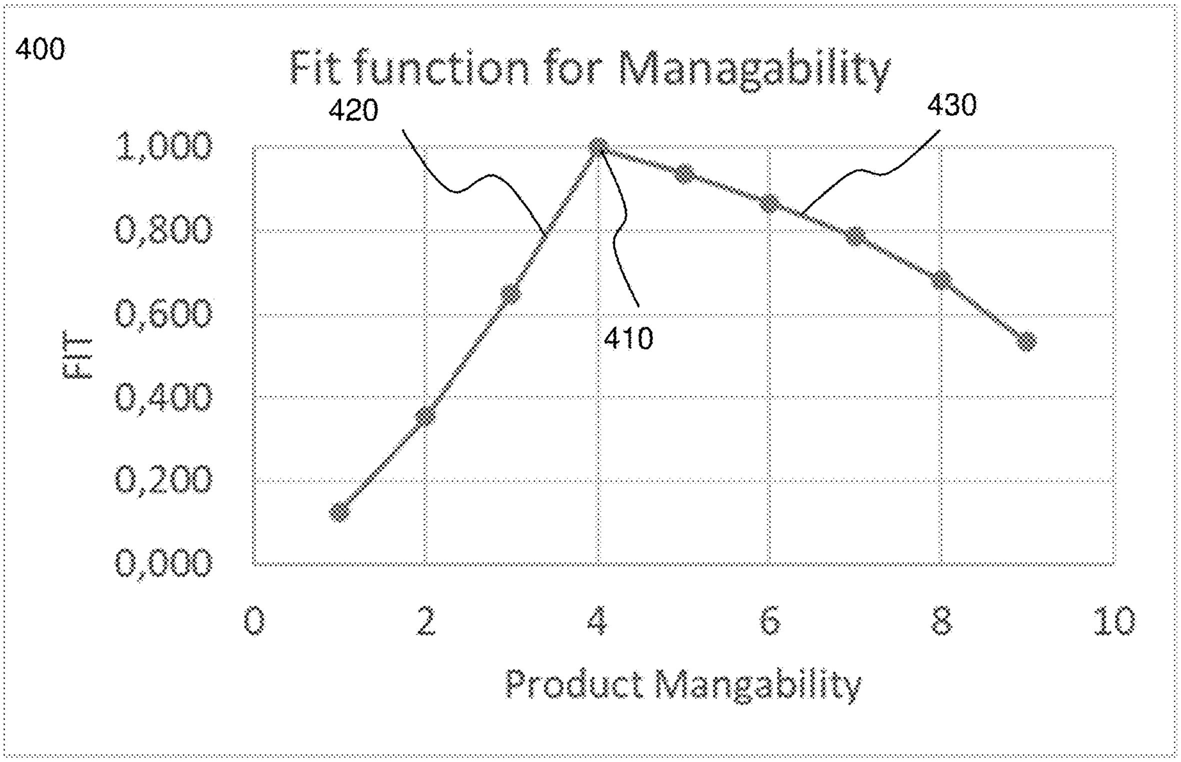

The distance function calculates the distance between the target and each product found in the database storing the Where LP is the lower exponent and UP is the upper exponent, and LP and UP are variables that change depending on users answers, e.g. ethnicity and goal choices Reference is made to FIG. 4, illustrating the output 400 by the fit-to-manageability function Fit( ).

The fit-to-manageability function presents a peak value 410 of 1 and a rate of decay 420 and 430. This value corresponds to the chemical compound having the best fit of manageability. Other values decrease rapidly with the LP and UP variables. The rate of decay 420 is influenced by the variable LP. The rate of decay 430 is influenced by the variable UP.

The method may vary the LP and UP values so as to modify the sensitivity of the fitting. If the product manageability is three (which is located lower than the target four where the fit-to-manageability function presents its peak), the fit score lower as compared to a score of five (which is located higher than the target four).

This is because depending on the profile, a higher manageability will be more preferable than a lower manageability. This is the case, for instance, in the situation where a person wishes to have smoother hair by usage of conditioner; the higher manageability will give a better conditioning effect than one with a lower manageability. However, too much conditioning will lead to heaviness and negative hair feel.

The converse is also true e.g. lower conditioning would be more preferable than a higher conditioning. e.g. in the situation where a person is looking for volume effect on hair, giving a higher manageability product will weigh the hair down more, leading to loss of hair volume.

The method thus has the liberty of modifying the LP and UP variables on a per-user basis. In general, in the event a product with the target manageability value of 6 is not available (fit=1), but a product of 5 and 7 is available, usually a 7 is more preferred to a 5. For example, if a Caucasian has volumizing goal active (the intent is to have voluminous hair), having a 5 is more preferable to enable more voluminous hair than a 7, because too much conditioning makes the hair have less volume. This is especially for fine hair typically found in Caucasian hair. In the case of an Asian or Latin American ethnicity, the hair is coarser, and requires more conditioning. Even if volumizing goal is chosen, exponents that make a 7 preferable to a 5 will be chosen.

An example is further discussed with reference to FIGS. 5 and 6.

Figure 5:
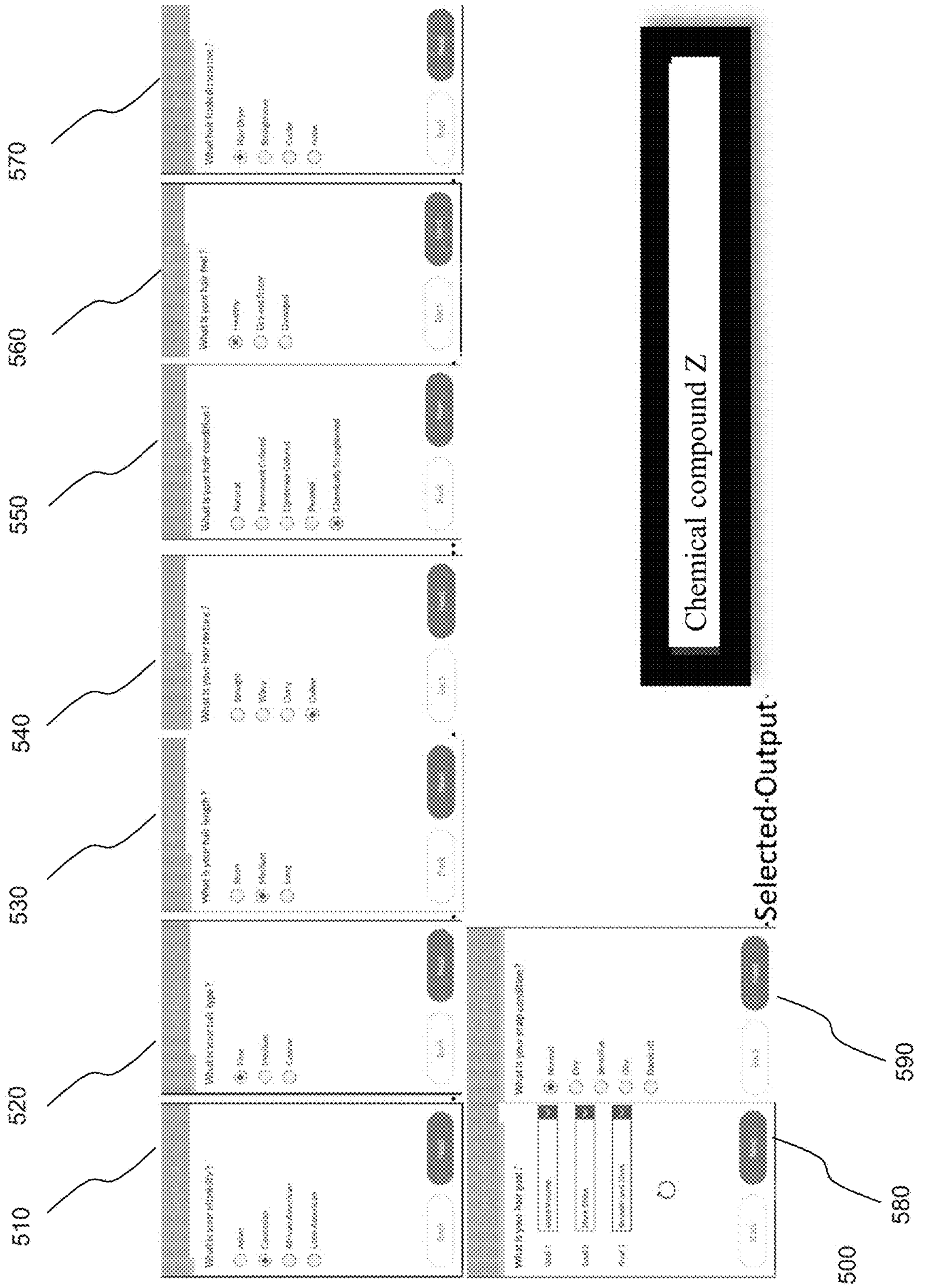

FIG. 5 is a screenshot of interface screens 500 presenting nine questions (510-590) to a user A.

Figure 6:
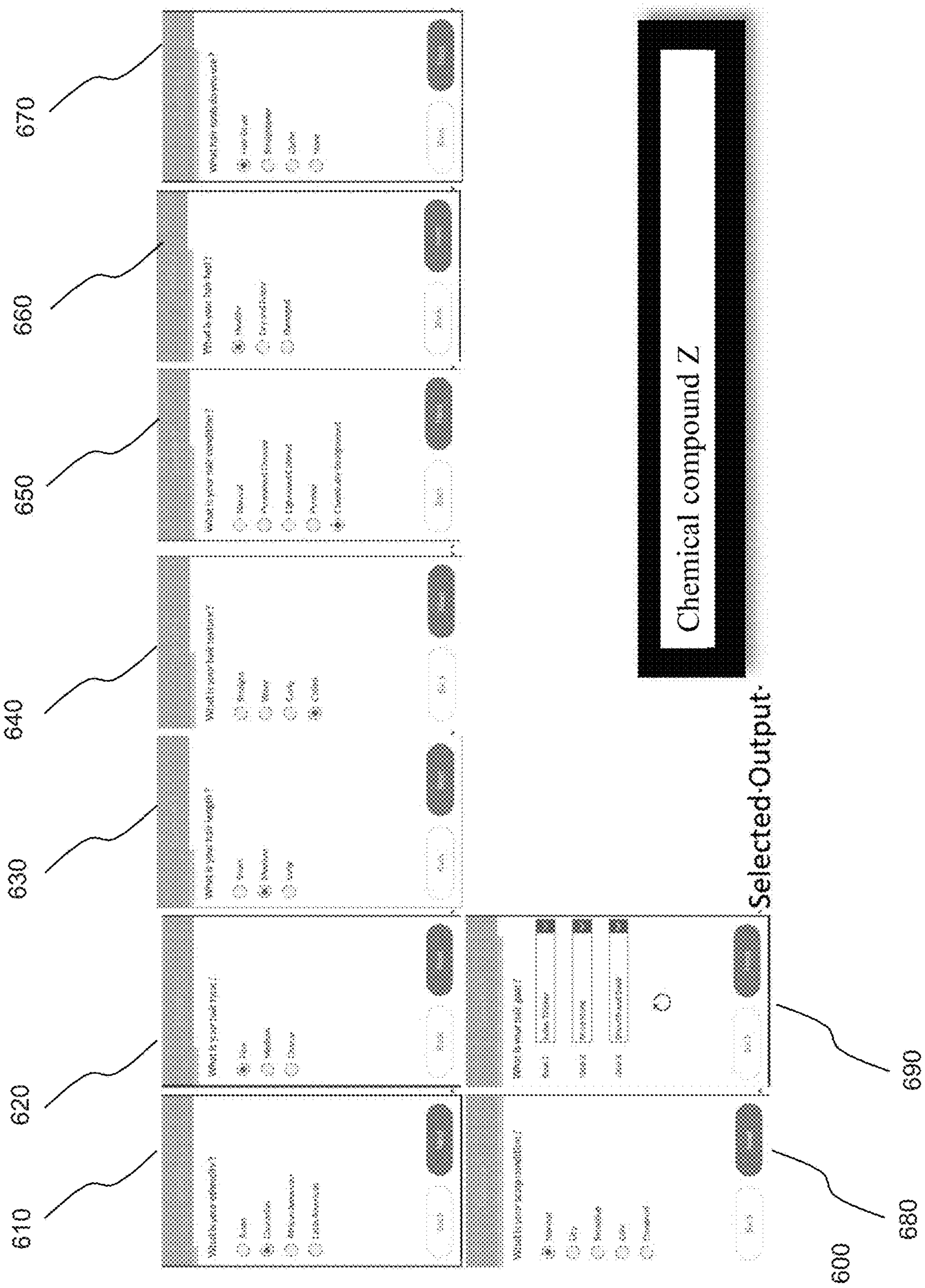

FIG. 6 is a screenshot of interface screens 600 presenting nine questions (610-690) to a user B. The questions presented to users A and B are the same, except for the first choice of goal in Question 8. In Example A, the first goal is More Volume, while in Example B, the first goal is Fuller Thicker hair.

Table XI illustrates the hair target properties.

The Conditioner ManageabilityTarget in both cases is set to 3. That means that 3 is the ideal conditioner manageability value, and would have a fit to manageability of 1.0.

To show the effect of LP, consider the fit to manageability value of the same Product X in user A vs user B.

Assume a Conditioner Manageability ScoreTarget (or goal) of 3 and a Conditioner Manageability$_{Product}$ of 2.

TABLE XI

| User | Conditioner Manageability Score$_{Target}$ | Conditioner Manageability$_{Product}$ | Volume Cosen | LP | Fit to Manageability |
|---|---|---|---|---|---|
| User A | 3 | 2 | Yes | 1.35 | $= (0.667)^{1.35}$ $= 0.868$ |
| User B | 3 | 2 | No | 0.35 | $= (0.667)^{0.35}$ $= 0.578$ |

From the above table, when Volume goal is chosen, a difference in LP value can change the fit to Manageability. Therefore a product which has a lower Conditioner ManageabilityProduct than Conditioner Manageability ScoreTarget has a higher fit for user A than user B Assume a Conditioner Manageabiity ScoreTarget of 3 and a Conditioner ManageabilityProduct of 4.

Table XII illustrates conditioner manageability target properties.

TABLE XII

| User | Conditioner Manageability Score$_{Target}$ | Conditioner Manageability$_{Product}$ | Volume Cosen | UP | Fit to Manageability |
|---|---|---|---|---|---|
| User A | 3 | 2 | Yes | 0.35 | $= (0.857)^{0.35}$ $= 0.781$ |
| User B | 3 | 2 | No | 1.6 | $= (0.857)^{1.6}$ $= 0.947$ |

Figure 7:
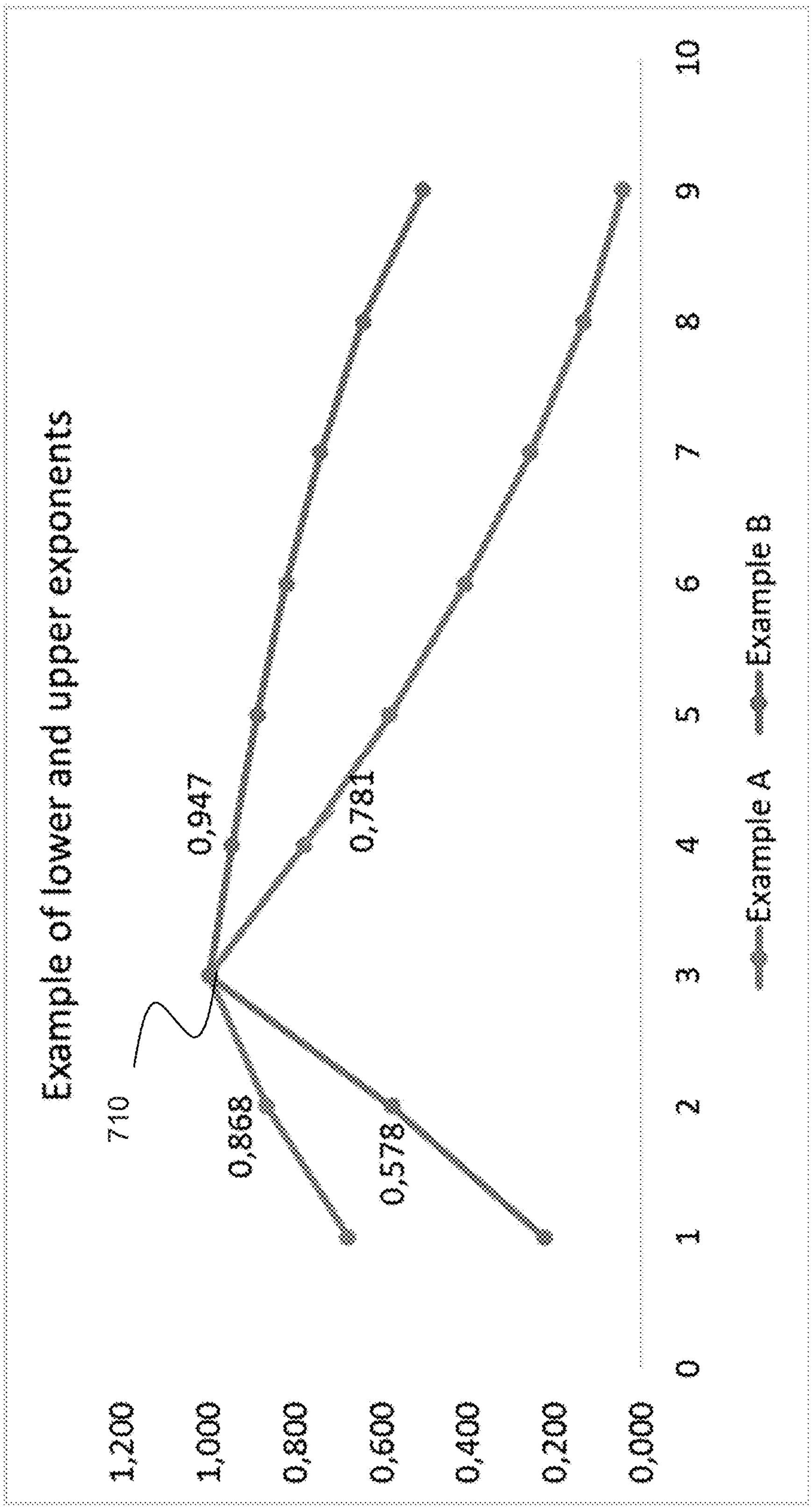

Conversely, when Volume goal is chosen, a product which has a higher Conditioner ManageabilityProduct than Conditioner Manageability ScoreTarget has a higher fit for user B than user A FIG. 7 illustrates an example of how the same chemical compound can have different fit to manageability value depending on the user.

The calculated Fit to manageability for user A is plotted as Example A. The plot of user B is plotted as Example B. The target is 3. The peak is the same peak 710 although with different decay rates.

The fit-to-goal function is further discussed.

The fit-to-goal functions determines the extent by which the chemical compound meets the computed goal scores. The formula is of the type:

$$\text{Fit to goal} = \sum \text{Weight}_i \times \text{Goal}_i \text{ where}$$

$$\text{Goal}_i = \begin{cases} 0, \text{ Goal Value}_{Product} \leq LSL \\ \dfrac{\text{Goal Value}_{Product}}{GoalThreshold_i}, \ LSL < \text{Goal Value}_{Product} < GoalThreshold_i \\ 1, \text{ Goal Value}_{Product} \geq GoalThreshold_i \end{cases}$$

Goal Value$_{Product}$ depends on the product properties. For instance. Color Protection Value$_{Product\ A}$ can be higher than Color Protection Value$_{Product\ B}$, because there is higher concentration of functional ingredient in A than in B that delivers that technical benefit or goal.

GoalThreshold$_i$ depends on the goal priority and varies between 0 to 1, e.g., a goal selected in Rank 1 will have a higher Goal Threshold value than a goal selected in Rank 3. In other words, GoalThreshold$_1$>GoalThreshold$_2$>GoalThreshold$_3$.

A goal in rank 1 will be more important to the user vs a goal in rank 3, and therefore more important to deliver on that technical benefit to the user.

A product with a higher fit to goal is therefore more able to meet the users needs.

Figure 8:
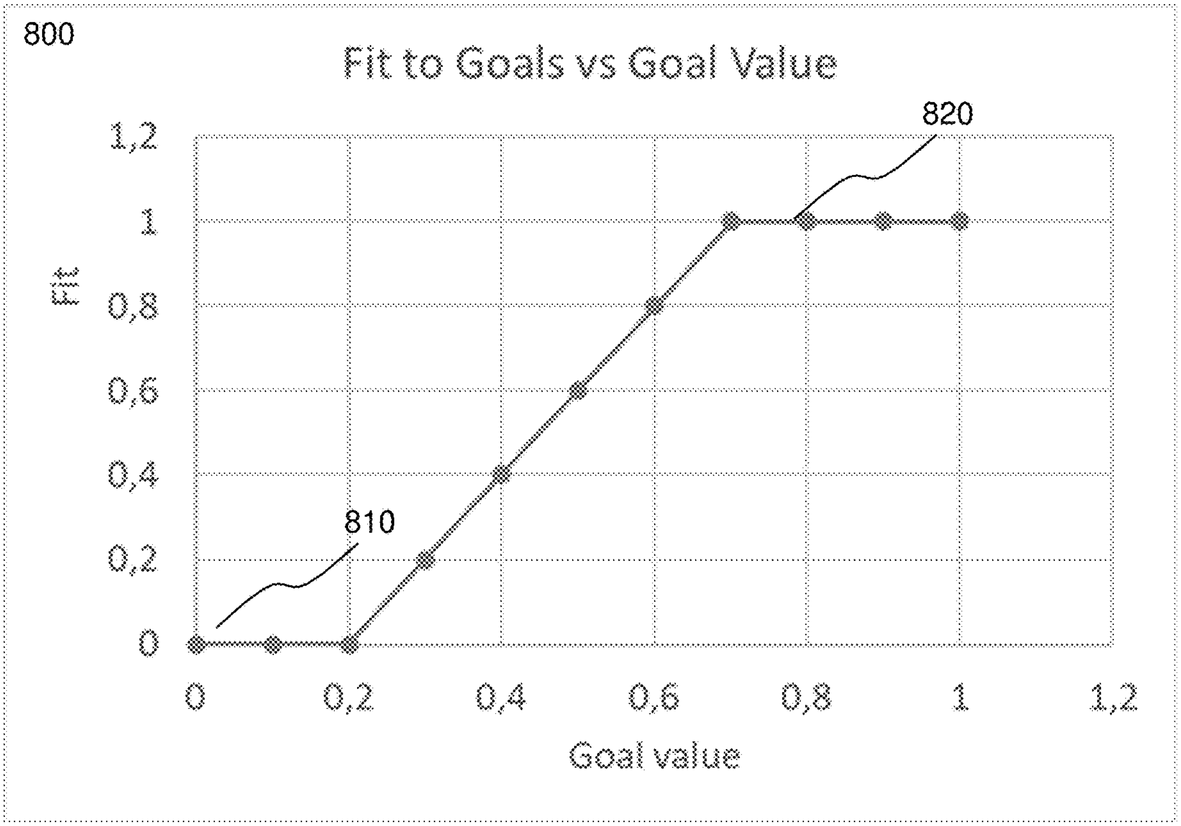

Reference is made to FIG. 8, illustrating the fit-to-goal function.

A chemical compound that does not contain a functional ingredient at a sufficient level (lower than the LSL) to deliver on a technical goal will have a fit value 810 of 0, and a product that has higher than the goal threshold value will have a fit value 820 of 1.

In general, most products are not formulated to achieve multiple technical benefits. However, by assigning different threshold values to each goal in order of importance, we are able to find a product that meets the overall user needs from a technical viewpoint.

The resulting chemical compounds are ranked according to the total score, and the method recommends the highest scoring chemical compound.

There is a benefit to determining the fit to goals using a fit function rather than using an average of product parameters or weighted average of product parameters.

A generic example is provided in Table XII, with the goal values for selected goals for 3 different products, and the calculation method.

An average takes the average value of the goals and finds the highest value, and recommends chemical compound A.

A weighted average may find the same chemical compound A.

The fit function using threshold values will find chemical compound C to be the best fit, as it has an ability to deliver on 3 goals as compared to chemical compound A and B.

TABLE XII

| Product Name | Goal 1 Most important | Goal 2 | Goal 3 Least important | Average | Weighted Average | Fit Function output |
|---|---|---|---|---|---|---|
| Product A | 0.1 | 0.6 | 0.9 | 0.53 | 0.41 | 0.50 |
| Product B | 0 | 0.3 | 1 | 0.43 | 0.29 | 0.50 |
| Product C | 0.2 | 0.4 | 0.6 | 0.40 | 0.34 | 0.70 |

The method may calculate an average score based on a weighted average of the fit to goal function and fit to Manageability function.

$$\text{Average Score} = A \times \text{Fit}_{Goal} + (1 - A) \times \text{Fit}_{Manageability};$$

Where A can vary between 0 to 1, more preferably between 0.4 to 0.6.

Hence, the method identifies a combination of products, from a variety of products, that best fits a particular users profile and needs.

The method identifies two main areas to obtain the best combination of chemical compounds for a particular user, which are the overall manageability of hair, and the technical benefits to deliver to the hair and/or scalp. This is particularly relevant when the chemical compounds are hair care chemical compounds, which are not made to deliver on multiple technical benefits. Certain combinations of technical benefits may be at conflict or opposites with each other.

In addition, as there are multiple hair types, different ethnicities, and a variety of damage levels, it is not practical to develop a formula for each profile of user.

As such, the method uses the fit-to-manageability function to find the product that best meet the manageability needs, from a variety of chemical compounds.

By utilizing a fit-to-goal function that uses threshold values for technical benefits, coupled with a fit-to-manageability function that finds the best fit for manageability, the method can find a chemical compound that best meets the user's desired goals on a holistic manner.

The invention claimed is:

1. A computer-implemented method for selecting a chemical compound applicable on a class of human hairs, the class of human hairs being constrained by hair properties, the method comprising:

obtaining (S10) a database storing data relative to chemical compounds applicable on the class of human hairs, for each compound the data comprising:

an identifier, an ingredient, and a performance score of the chemical compound when applied on human hairs, the performance score comprising a manageability score and a goal score;

obtaining (S20), from user input, assessed hair properties and hair target properties;

computing (S30) at least one goal score and a manageability goal score from the assessed hair properties and hair target properties, the computed goal score and the computed manageability goal score thereby forming a signature;

determining (S40) at least one identifier of a chemical compound stored in the database corresponding to a chemical compound satisfying the computed goal score and the computed manageability goal score, the satisfying comprising minimizing a distance function between the computed goal score and a corresponding goal score and maximizing a fit-to-manageability function between the computed manageability goal score and the corresponding manageability score;

outputting (S50) the determined at least one identifier of the chemical compound to be applied on the human hairs;

selecting the chemical compound of the at least one identifier;

applying the selected chemical compound to the human hair to provide the hair target properties; wherein the assessed hair properties and/or hair target properties comprise one or more of a hair type criterion including straight hair, wavy hair, curly hair or coily hair, a hair length criterion of short, medium or long, a hair condition criterion including untreated, colored, permed or bleached hair, a hair feel criterion associated with virgin hair or with chemically or heat treated hair, hair tool use criterion, a hair goal criterion including color protection, repair, shine, smooth, a scalp condition criterion including oily, dandruff, dry, a scalp goal criterion including sebum control, anti-dandruff and moisturize, a hair texture criterion, a hair diameter criterion including fine, medium and coarse, degree of damage criterion and/or a hair diameter of fine hair of 50 to 70 mm diameter, medium hair of 70 to 90 mm diameter and coarse hair of 90 to 120 mm diameter; and the selected chemical compound applicable to human hairs comprise one or more of a shampoo compound and/or a hair conditioner compound; and, wherein the distance function for the shampoo compound and/or the hair conditioner compound is determined according to:

a shampoo compound distance term of the type:

$$(\text{Cleansing Score Product} - \text{Cleansing Score target})^2 + (\text{Shampoo Manageability Product} - \text{Shampoo Manageability Score target})^2 ;$$

a conditioner compound distance term of the type:

Conditioner Manageability Product-Conditioner Score target; or a treatment distance term of the type:

Treatment Manageability Product-Treatment Score target;

wherein:

Cleansing Score Product, is a variable representing a value of a cleansing goal score by the chemical compound;

Shampoo Manageability Product is a variable representing a value of a goal score of a shampooing manageability by the chemical compound;

Treatment Manageability Product is a variable representing a value of a goal score of a treatment manageability by the chemical compound;

Cleansing Score Target is a variable representing a value of a cleansing goal score computed from the assessed hair properties;

Treatment Score Target is a variable representing a value of a treatment goal score computed from the assessed hair properties and hair target properties;

Shampoo Manageability Score Target is a variable representing a value of a shampoo manageability goal score computed from the assessed hair properties and hair target properties; and Conditioner Manageability product is a variable representing a value of a conditioner manageability goal score computed from the assessed hair properties and hair target properties.

2. The method of claim 1 wherein the distance function is a function taking the computed goal score and the corresponding goal score as input, and outputting a decreasing value as the distance between the computed goal score and the corresponding goal score decreases.

3. The method of claim 1 wherein the fit-to-manageability function is function of the type:

$$\text{Fit(Manageablility)} = \{(\text{Manageability Product} - LSL)^{LP}$$

$$\text{Manageability Score} - LSL'\left(\frac{USL - \text{Manageability Prodcut}}{USL - \text{Manageability Score}}\right)^{up}$$

and

Manageability Product≤Manageability Score

Manageability Product>Manageability Score wherein:

Manageability is a vector comprising Manageability Product variable and a Manageability Score variable, where Manageability Product is a variable representing a value of a manageability score by the chemical compound and a Manageability Score is a variable representing a value of a manageability goal score computed from the assessed hair properties and hair target properties; and LSL is a first variable and USL is a second variable;

LP is a lower exponent variable depending on user input and UP is an upper exponent variable depending on user input.

4. The method of claim 1, wherein outputting (S50) the determined at least one identifier of the chemical compound comprises averaging the computed goal score and the computed manageability score, the at least one identifier of the chemical compound being ranked according to a fit-to-goal distance to the average.

5. The method of claim 4, wherein the fit-to-goal distance comprises a function of the type:

$$\text{Fit to goal} = L\text{Weight}_i \times \text{Goal}_i$$

where $$\text{Goal}_i = \begin{cases} 0, \text{Goal } ValueProduct \le LSL \\ \dfrac{\text{Goal } ValueProduct}{GoalThreshold}, LSL < Goal\ ValueProduct < GoalThreshold_i; \\ 1, \text{Goal } ValueProdcut \ge GoalThreshold_i \end{cases}$$

wherein:

$\text{Goal}_i$ is a value representing a goal score;

Goal ValueProduct is a variable representing a value of the performance score;

$\text{GoalThreshold}_i$ is a variable representing a value of a goal priority, varying between 0 to 1; and $\text{Weight}_i$ is a predetermined weight.

6. The method of claim 1 wherein outputting (S50) the determined at least one identifier of the chemical compound further comprises displaying the at least one identifier of the chemical compound on a display engine.

7. The method of claim 1, further comprising applying the chemical compound on human hairs of a class corresponding to the assessed hair properties the chemical compound identified by the output, thereby reaching the hair target properties obtained from the user input.

8. The method of claim 1 wherein the chemical compounds applicable on human hairs comprise one or more of a shampoo, a hair conditioner, a hair oil, a scalp tonic and/or serum.

* * * * *